(12) United States Patent  (10) Patent No.: US 6,321,125 B1
Kuzma  (45) Date of Patent: *Nov. 20, 2001

(54) COCHLEAR ELECTRODE SYSTEM INCLUDING DISTALLY ATTACHED FLEXIBLE POSITIONER

(75) Inventor: Janusz A. Kuzma, Englewood, CO (US)

(73) Assignee: Advanced Bionics Corporation, Sylmar, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/443,628

(22) Filed: Nov. 19, 1999

Related U.S. Application Data

(63) Continuation-in-part of application No. 09/140,034, filed on Aug. 26, 1998, now Pat. No. 6,038,484.

(51) Int. Cl.$^7$ ........................................................ A61N 1/05
(52) U.S. Cl. .................................................................. 607/137
(58) Field of Search ............................... 607/137, 55–57; 606/129, 108; 600/379, 585

(56) References Cited

U.S. PATENT DOCUMENTS

| | | |
|---|---|---|
| 4,809,712 | 3/1989 | Kuzma . |
| 4,819,647 | 4/1989 | Byers et al. . |
| 5,545,200 | * 8/1996 | West et al. ............................ 607/122 |
| 5,545,219 | 8/1996 | Kuzma . |
| 5,578,084 | 11/1996 | Kuzma et al. . |
| 5,645,585 | 7/1997 | Kuzma . |
| 5,649,970 | 7/1997 | Loeb et al. . |
| 5,800,500 | 9/1998 | Spelman et al. . |
| 5,833,714 | 11/1998 | Loeb . |
| 5,902,331 | * 5/1999 | Bonner et al. ........................ 607/122 |
| 5,999,859 | * 12/1999 | Jolly ..................................... 607/137 |
| 6,038,484 | * 3/2000 | Kuzma ................................. 607/137 |
| 6,195,586 | * 2/2001 | Kuzma ................................. 607/137 |

* cited by examiner

Primary Examiner—George R. Evanisko
(74) Attorney, Agent, or Firm—Bryant R. Gold

(57) ABSTRACT

An electrode system adapted for insertion into a human cochlea as part of a cochlear stimulation system includes (1) an electrode array, made in a straight or curved shape, but made on a flexible carrier so that it can easily bend within a curved body cavity, such as the cochlea; and (2) a flexible positioner, molded in a curved or straight shape from a silicone polymer so as to make it easy to slide into the body cavity. A distal tip of the positioner is attached to the electrode array at a location that is proximal from the distal end of the electrode array about 3–5 mm. An insertion tube facilitates insertion of the electrode system into a human cochlea in one operation with the aid of a movable stylet wire. One embodiment of the positioner includes keeper tabs at its distal end, and side walls at its proximal end, to help maintain the positioner in a desired position along the back side of the electrode array during and after the insertion process.

19 Claims, 22 Drawing Sheets

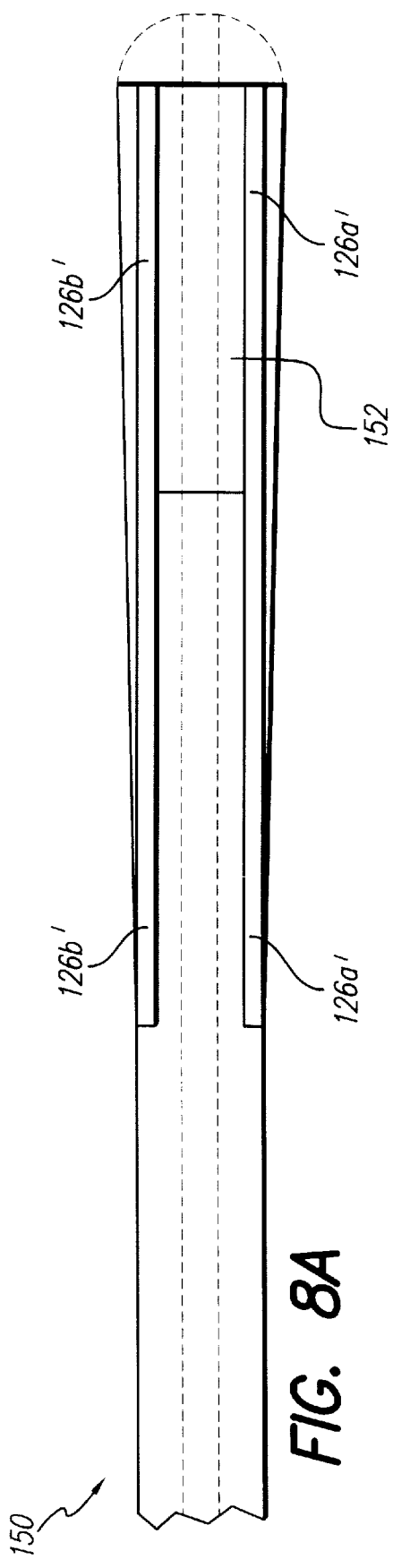
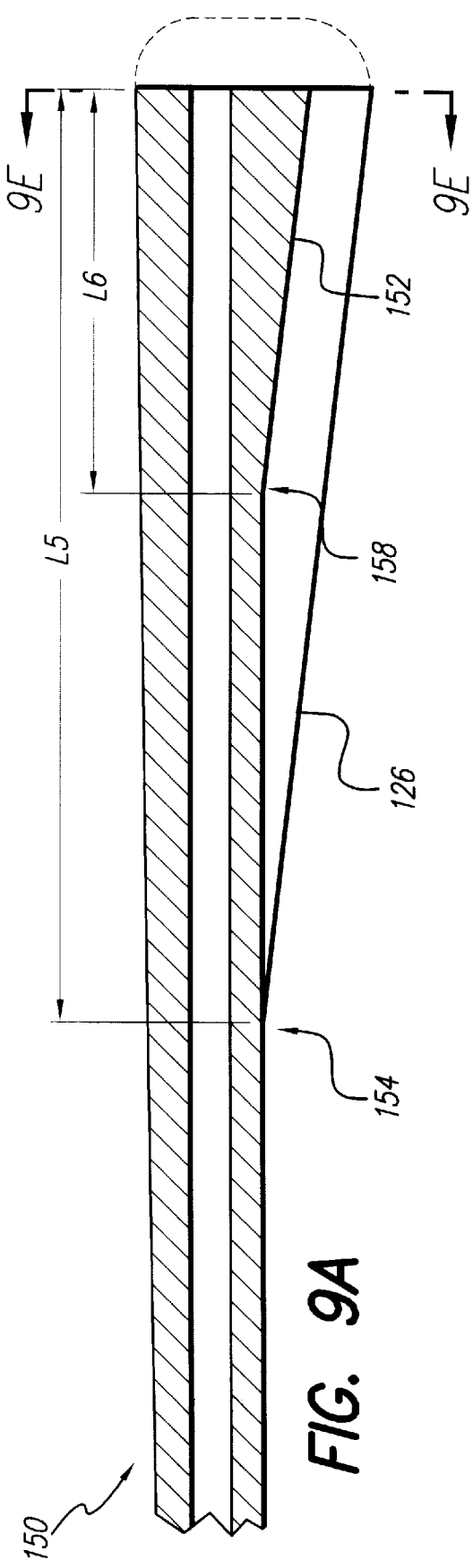

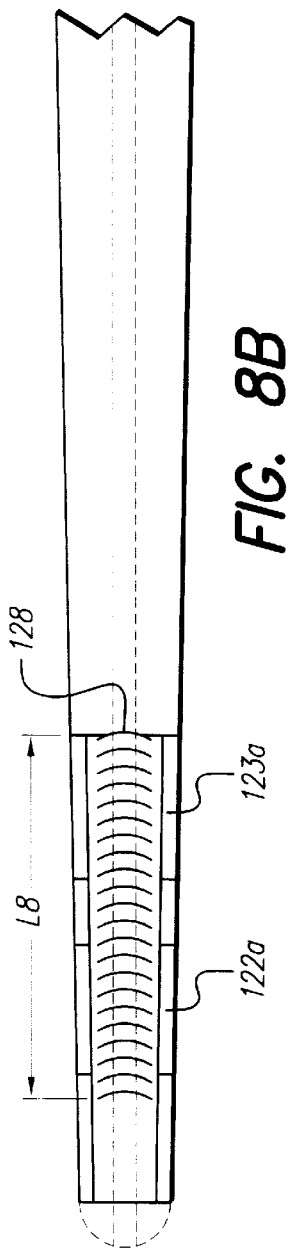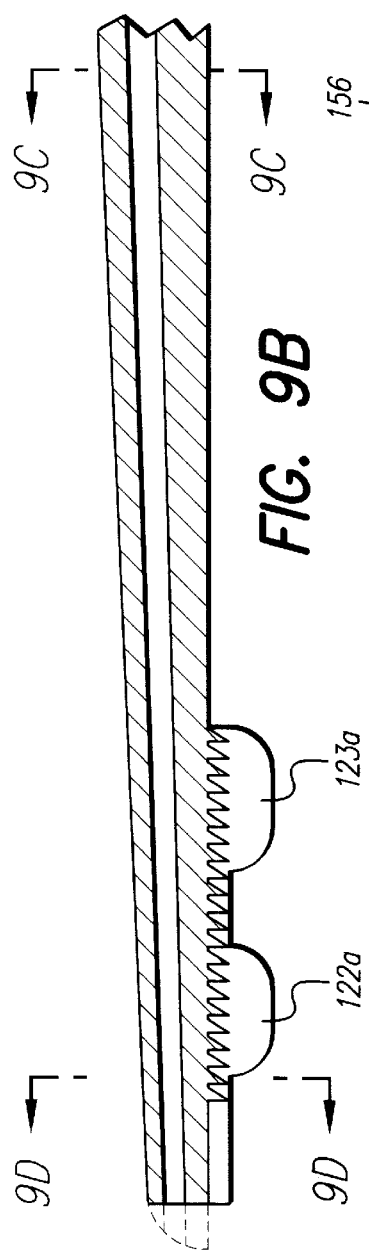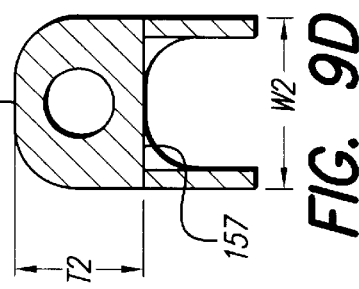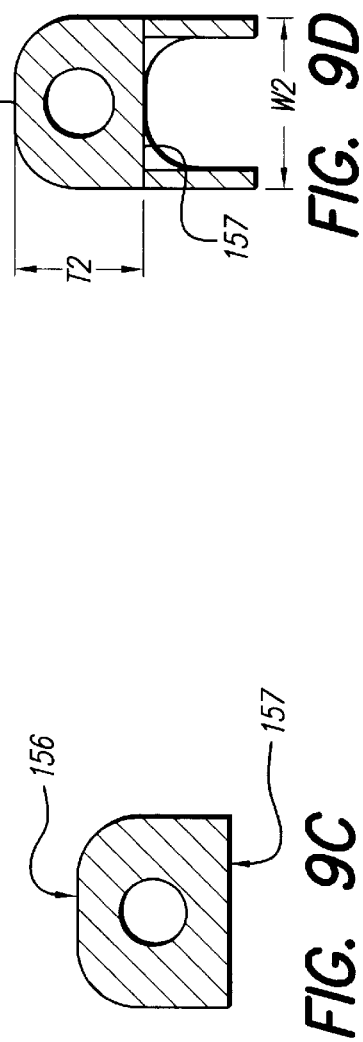

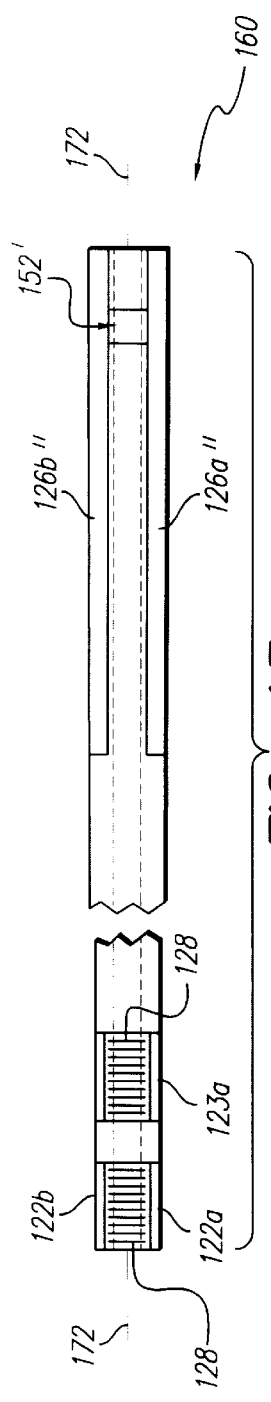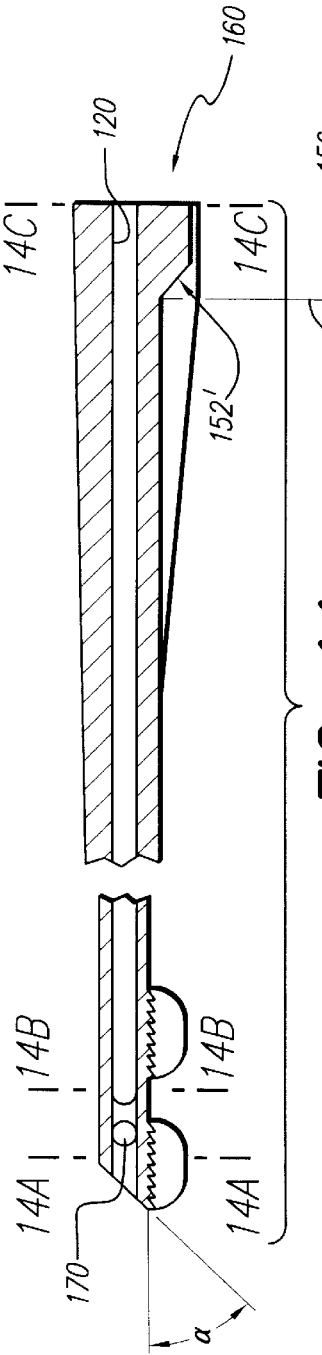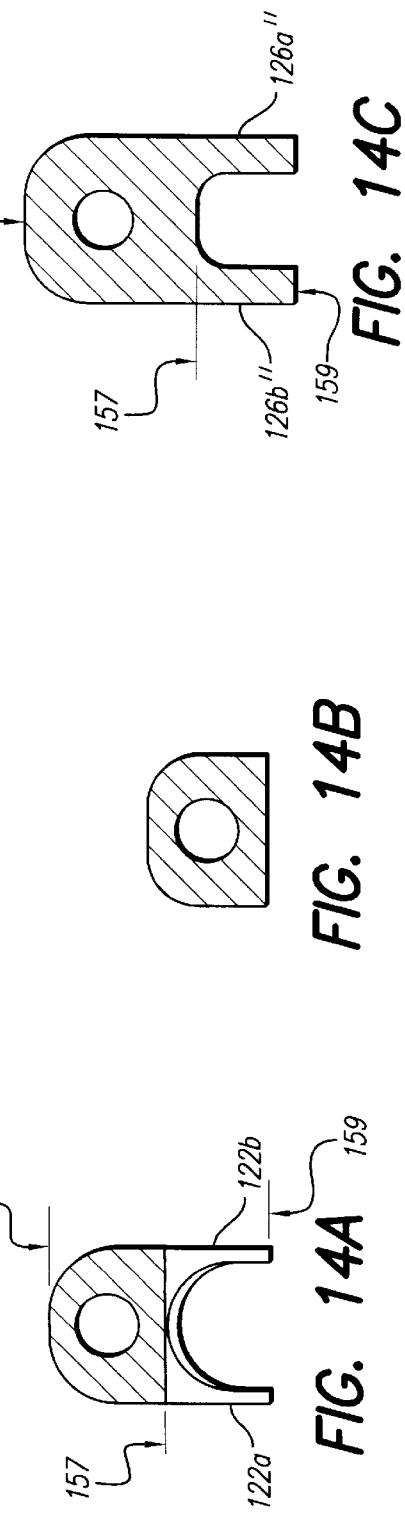

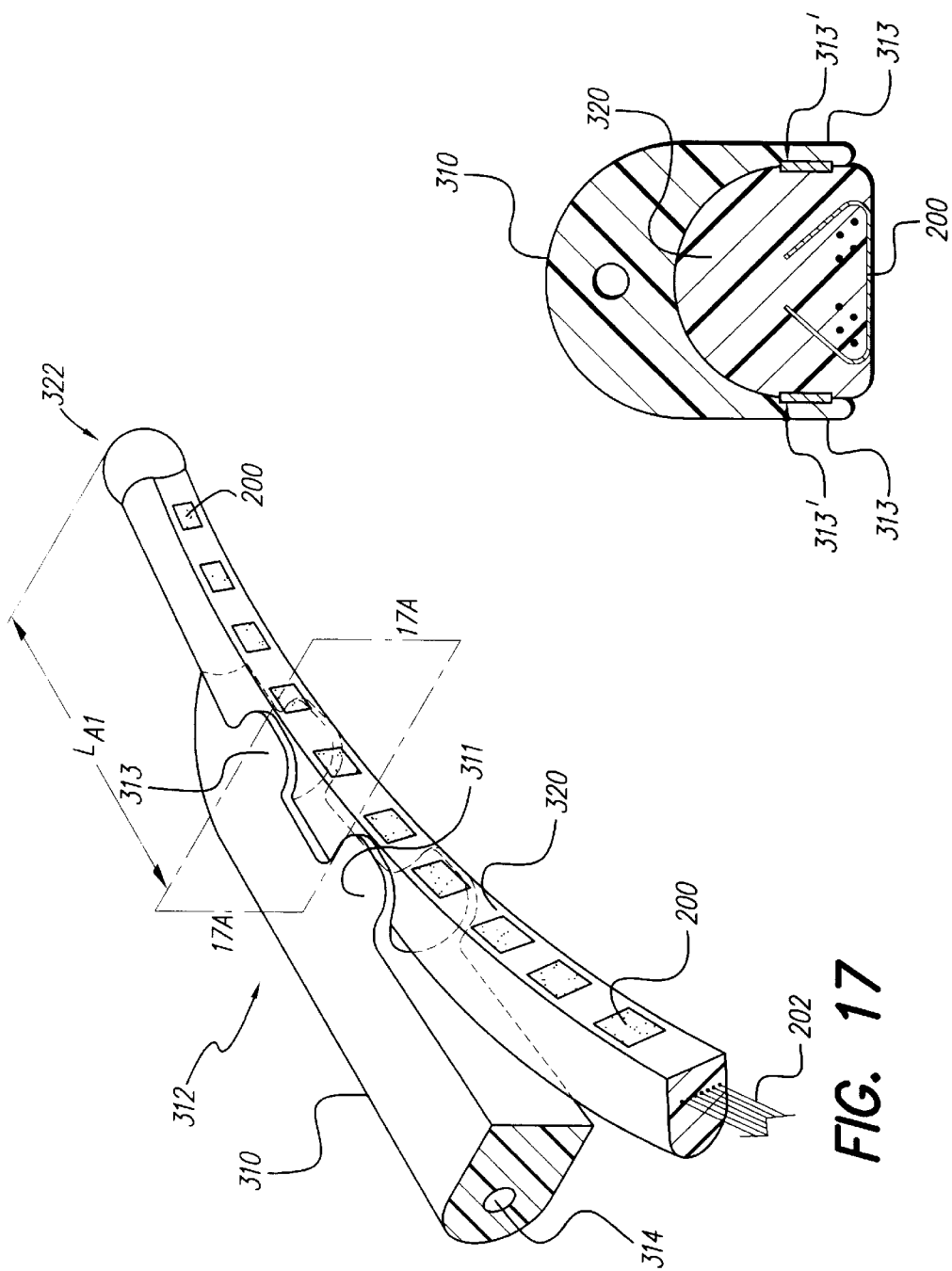

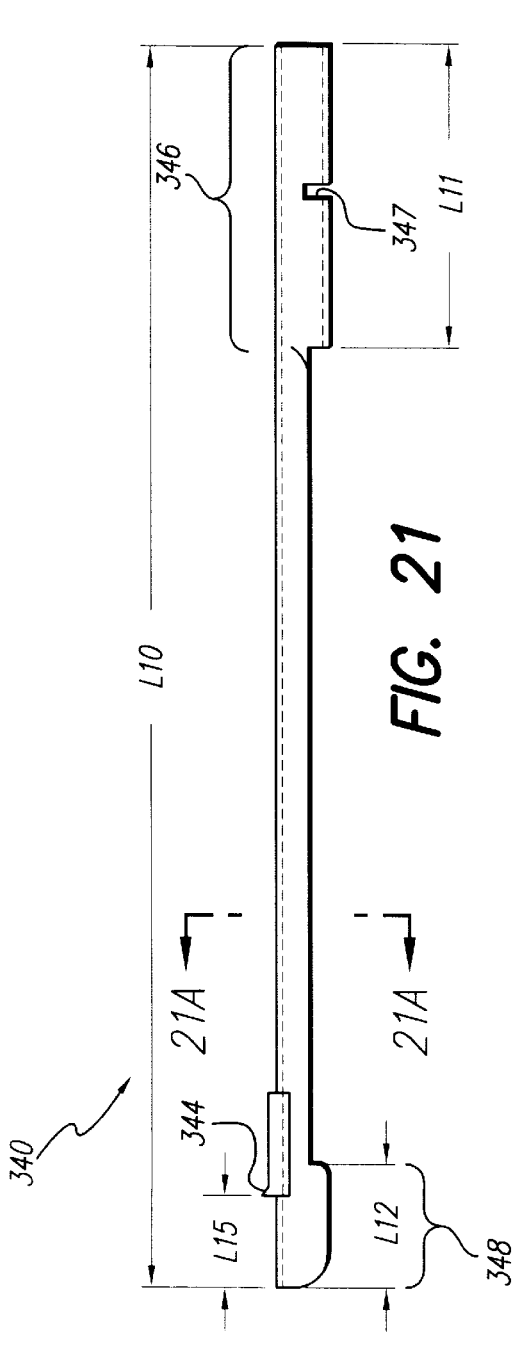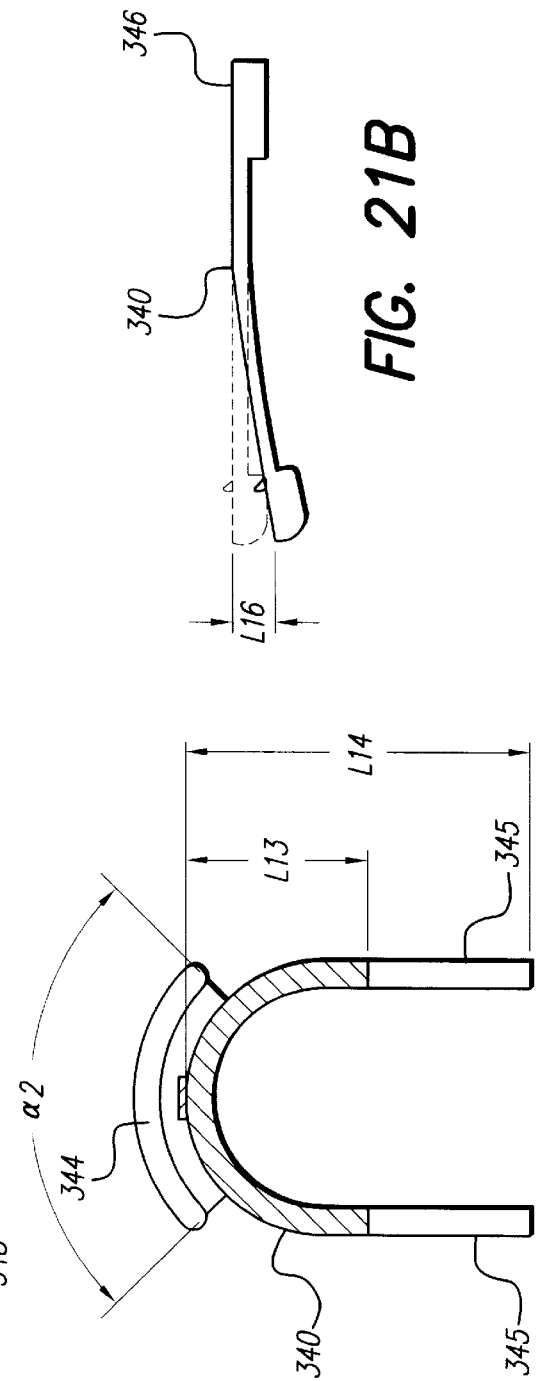

COCHLEAR ELECTRODE SYSTEM INCLUDING DISTALLY ATTACHED FLEXIBLE POSITIONER

This application is a continuation-in-part (CIP) of U.S. patent application Ser. No. 09/140,034, filed Aug. 26, 1998, now U.S. Pat. No. 6,038,484, which patent is incorporated herein by reference.

BACKGROUND OF THE INVENTION

The present invention relates to implantable stimulation devices, e.g., cochlear prosthesis used to electrically stimulate the auditory nerve, and more particularly to an electrode array for use with a cochlear stimulator that is designed to hug the modiolus so as to place electrode contacts of the electrode array in close proximity to the ganglion cells and thereby to the auditory nerve fibers.

Hearing loss, which may be due to many different causes, is generally of two types: conductive and sensorineural. Of these, conductive hearing loss occurs where the normal mechanical pathways for sound to reach the hair cells in the cochlea are impeded, for example, by damage to the ossicles. Conductive hearing loss may often be helped by use of conventional hearing aids, which amplify sound so that acoustic information does reach the cochlea and the hair cells. Some types of conductive hearing loss are also amenable to alleviation by surgical procedures.

In many people who are profoundly deaf, however, the reason for their deafness is sensorineural hearing loss. This type of hearing loss is due to the absence or the destruction of the hair cells in the cochlea which are needed to transduce acoustic signals into auditory nerve impulses. These people are unable to derive any benefit from conventional hearing aid systems, no matter how loud the acoustic stimulus is made, because their mechanisms for transducing sound energy into auditory nerve impulses have been damaged. Thus, in the absence of properly functioning hair cells, there is no way auditory nerve impulses can be generated directly from sounds.

To overcome sensorineural deafness, there have been developed numerous cochlear implant systems—or cochlear prosthesis—which seek to bypass the hair cells in the cochlear (the hair cells are located in the vicinity of the radially outer wall of the cochlea) by presenting electrical stimulation to the auditory nerve fibers directly, leading to the perception of sound in the brain and an at least partial restoration of hearing function. The common denominator in most of these cochlear prosthesis systems has been the implantation into the cochlea of electrodes which are responsive to suitable external source of electrical stimuli and which are intended to transmit those stimuli to the ganglion cells and thereby to the auditory nerve fibers.

A cochlear prosthesis operates by direct electrical stimulation of the auditory nerve cells, bypassing the defective cochlear hair cells that normally transduce acoustic energy into electrical activity in such nerve cells. In addition to stimulating the nerve cells, the electronic circuitry and the electrode array of the cochlear prosthesis performs the function of the separating the acoustic signal into a number of parallel channels of information, each representing the intensity of a narrow band of frequencies within the acoustic spectrum. Ideally, each channel of information would be conveyed selectively to the subset of auditory nerve cells that normally transmitted information about that frequency band to the brain. Those nerve cells are arranged in an orderly tonotopic sequence, from high frequencies at the basal end of the cochlear spiral to progressively lower frequencies towards the apex. In practice, this goal tends to be difficult to realize because of the anatomy of the cochlea.

Over the past several years, a consensus has generally emerged that the scala tympani, one of the three parallel ducts that, in parallel, make up the spiral-shaped cochlea, provides the best location for implantation of an electrode array used with a cochlear prosthesis. The electrode array to be implanted in this site typically consists of a thin, elongated, flexible carrier containing several longitudinally disposed and separately connected stimulating electrode contacts, perhaps 6–30 in number. Such electrode array is pushed into the scala tympani duct to a depth of about 20–30 mm via a surgical opening made in the round window at the basal end of the duct. During use, electrical current is passed into the fluids and tissues immediately surrounding the individual electrical contacts in order to create transient potential gradients that, if sufficiently strong, cause the nearby auditory nerve fibers to generate action potentials. The auditory nerve fibers arise from cell bodies located in the spiral ganglion, which lies in the bone, or modiolus, adjacent to the scala tympani on the inside wall of its spiral course. Because the density of electrical current flowing through volume conductors such as tissues and fluids tends to be highest near the electrode contact that is the source of such current, stimulation at one contact site tends to activate selectively those spiral ganglion cells and their auditory nerve fibers that are closest to that contact site. Thus, there is a need for the electrode contacts to be positioned as close to the ganglion cells as possible. This means, in practice, that the electrode array, after implant, should preferably hug the modiolar wall, and that the individual electrodes of the electrode array should be positioned on or near that surface of the electrode array which is closest to the modiolar wall.

In order to address the above need, it is known in the art to make an intracochlear electrode array that includes a spiral-shaped resilient carrier which generally has a natural spiral shape so that it better conforms to the shape of the scala tympani. See, e.g., U.S. Pat. No. 4,819,647. The '647 U.S. patent is incorporated herein by reference. Unfortunately, while the electrode shown in the '647 patent represents a significant advance in the art, there exists lack of sufficient shape memory associated with the electrode to allow it to return to its original curvature (once having been straightened for initial insertion) with sufficient hugging force to allow it to wrap snugly against the modiolus of the cochlea.

It is also known in the art, as shown in applicant's prior patents, U.S. Pat. Nos. 5,545,219 and 5,645,585, to construct an electrode carrier from two initially straight members, a rodlike electrode carrier and a flexible rodlike positioning member. As shown in these patents, the two members extend in substantially parallel relation to and closely alongside each other, but are connected to each other only at their respective leading and trailing end regions. After implant, a pushing force is applied to the positioning member so that it is forced to assume an outwardly arched configuration relative to the electrode carrier, thereby forcing the electrode carrier into a close hugging engagement with the modiolus, thereby placing the electrode contacts of the electrodes in as close a juxtaposition to the cells of the spiral ganglion as possible. The '219 and '585 U.S. patents are also incorporated herein by reference.

Unfortunately, while the electrode array taught in the above-referenced '219 and '585 patents has the right idea, i.e., to force the electrode carrier into a close hugging engagement with the modiolus, it does so only by use of an additional element that makes manufacture of the lead more difficult and expensive, and only through application of an additional pushing force which is applied to an electrode structure after it is already fully inserted into the cochlea. Such additional pushing force may easily cause damage to the delicate scala tympani. Moreover, the entire electrode array may twist during the insertion process, or when the additional pushing force is applied, thereby causing the electrode contacts to twist and/or be forced away from the modiolus, rather than in a hugging relationship therewith.

Thus, while it has long been known that an enhanced performance of a cochlear implant can be achieved by proper placement of the electrode contacts close to the modiolar wall of the cochlea, two main problems have faced designers in attempting to achieve this goal. First, it is extremely difficult to assemble electrode contacts on the medial side of the an electrode array, facing the modiolus of the cochlea. Second, heretofore there has either been the need for application of an external (and perhaps unsafe) force, or a lack of sufficient shape memory, to allow the electrode (after initial straightening to facilitate insertion) to assume or return to the desired curvature needed to place the electrodes against the modiolar wall so that the curvature wraps snugly around the modiolus of the cochlea. As a result, the electrode contacts of the prior art electrodes are generally positioned too far way from the modiolar wall.

It is thus evident that improvements are still needed in cochlear electrodes, particularly to facilitate assembling an electrode so that the electrode contacts are on the medial side of the electrode array, and to better assure that the electrode assumes a close hugging relationship with the modiolus once implantation of the electrode has occurred.

SUMMARY OF THE INVENTION

The present invention addresses the above and other needs by providing an electrode system that allows for correct positioning of the electrode contacts against the modiolar wall of the cochlea. Such "correct" positioning is achieved through the use of an electrode system that includes the following main components: (1) an electrode array, made in a straight or slightly curved shape on a flexible carrier so that it can easily bend within the cochlea; (2) a flexible positioner, typically molded from a silicone polymer so as to make it easy to slide into the cochlea; and (3) a insert tool, or guide tube, that allows the electrode array and/or the positioner, to be easily inserted into the cochlea.

It is an aspect of the invention to provide an electrode system for use with a cochlear stimulation system that fills the cochlea, i.e., that places electrode contacts of the electrode array adjacent the modiolar wall of the cochlea while at the same time filling the space behind the electrode array so that the electrode contacts must remain in their desired position adjacent the modiolar wall.

In a preferred embodiment, the positioner is attached at its distal end to the electrode array at an attachment point that is near, but not at, the distal end of the electrode array. The positioner is attached at an attachment point that is approximately 3–5 mm from the distal tip of the electrode array. Advantageously, such electrode array with distally-attached positioner may be readily inserted into the cochlea in one easy-to-perform operation. Insertion is achieved by first making a cochleostomy of the proper dimensions, loading the electrode array with distally-attached positioner into an insertion tube, inserting a distal end of the electrode system and insertion tube through the cochleostomy, and then gently pushing the system into the cochlea using an extendable stylet wire threaded into a longitudinal passageway that passes through the length of the positioner. Having the distal tip of the electrode array extend beyond the point to which the distal tip of the positioner is attached allows the soft flexible of the electrode array to easily maneuver itself through the bends of the spiraling scala tympani duct of the cochlea and thereafter pull the electrode through such bends without inflicting damage to the delicate cochlear structure, i.e., without puncturing the delicate tissue membranes that define the scala tympani.

In another embodiment, the electrode system includes detached components (i.e., an electrode array that is separate—not attached—to the positioner) and the insertion of the electrode system is performed in three main steps. First, the flexible positioner is inserted through the appropriate dimension of cochleostomy. This means it is inserted into the scala tympani (one of the channels of the cochlea) to the desired depth. The desired depth typically involves a rotation of about 360 degrees and causes the positioner to rest against the outer or lateral wall of the scala tympani, leaving an opening slightly larger than the cross-section of the electrode array adjacent the inner wall of the scala tympani. Advantageously, the super-flexible nature of the positioner prevents it from causing damage to the cochlear structure. At the same time, once inserted, it provides a guide for the electrode, and protects the cochlear walls from being damaged or touched directly by the stiffer electrode body. Second, after insertion of the positioner to the desired depth, the guiding insert may be pushed into the opening of the cochlear. Third, the electrode array is inserted through the opening of the guiding insert to the desired depth. This desired depth is preferably beyond the depth of the positioner. The distal end of the array advantageously includes one or more engaging or locking barbs or teeth that engage with corresponding barbs or teeth at the distal end of the positioner. At this stage, the electrode is positioned very close to the modiolus of the cochlea. Then, as a final optimization of the position of the electrode contacts of the electrode array, the electrode array is pulled back slightly (about 2 mm). This backward motion assures that the distal tips of the electrode array and the positioner are engaged by the barbs located thereon. Such engagement may further serve to force the electrodes into direct contact with the modiolar wall.

In another embodiment, still using an electrode system that includes detached components, a similar procedure is followed, except that the electrode array is inserted into the cochlea first, and then the positioner is inserted through the guide tube so as to lie along a back side (i.e., the side opposite the electrode contacts) of the electrode array, thereby positioning the electrode contacts of the array near the modiolar wall. In such embodiment, the positioner advantageously has at least one pair of guide tabs, or wings, at or near its distal tip, so as to keep the distal tip of the positioner from slipping off of the distal tip of the electrode array. In other words, the tabs or wings at the distal tip of the positioner, form a channel, or groove, through which the body of the electrode array may slide as the positioner is inserted behind the electrode array, and which once inserted, keep the positioner distal tip in a desired position alongside (and, more particularly, along a back side of) the distal tip of the electrode array. In such embodiment, the positioner also may include a pair of flexible side walls near or at its proximal end. The space between such side walls also forms a channel or groove into which the body of the electrode array may be positioned as the positioner is slid into position alongside the electrode array within the cochlea. Such channel or groove may further include a sloping floor that acts as an additional spacer that pushes or forces a proximal end of the electrode array into close engagement with the basal end of the cochlea as the positioner is fully inserted into the cochlea.

In accordance with yet an additional embodiment of the invention, a cochlear electrode system is provided that includes (1) an electrode array and (2) an electrode positioner. Using a preferred insertion technique or method, the electrode array is first inserted into the cochlea as far as it reasonably can be; then the positioner is inserted into the cochlea, behind the electrode array so as to force or push the electrode contacts of the array against the modiolar wall. As required, a guide tube may be used to assist with inserting the electrode positioner into the cochlea. Moreover, as the positioner is thus inserted into the cochlea behind the electrode array, the positioner carries the electrode deeper into the cochlea, e.g., approximately ½ turn deeper. In such instance, the positioner need not be equipped with internal barbs at its distal end, but it may be.

It is one feature of the electrode system of the present invention that the electrode array is optimally positioned against the modiolar wall in a cochlea of any size.

It is another feature of the invention that insertion of the electrode array avoids or produces minimal trauma to the cochlear structure.

It is still another feature of the invention that the electrode system allows deep insertion of the electrode array beyond 360 degrees within the spiraling scala tympani duct of the cochlea.

It is yet an additional feature of the invention that the electrode system can be manufactured using easy-to-implement, low-cost, technology and manufacturing techniques.

BRIEF DESCRIPTION OF THE DRAWINGS

The above and other features and advantages of the present invention will be more apparent from the following more particular description thereof, presented in conjunction with the following drawings wherein:

FIG. 8A is a bottom view of the proximal end of the positioner of FIG. 7, looking at the side of the positioner that lies adjacent the electrode array when the positioner is inserted alongside the electrode array within the cochlea;

FIG. 8B is a bottom view of the distal end of the positioner of FIG. 7, looking at the side of the positioner that lies adjacent the electrode array when the positioner is inserted alongside the electrode array within the cochlea;

FIG. 13 is a bottom segmented view of another variation of a positioner that may be used with the present invention, looking at the side of the positioner that lies adjacent the electrode array when the positioner is inserted alongside the electrode array within the cochlea;

FIG. 14 is a side segmented section view, rotated 90° from the view shown in FIG. 13, of the positioner;

FIGS. 14A, 14B and 14C are sectional views, taken along the lines 14A—14A, 14B—14B, and 14C—14C of FIG. 14 respectively;

FIG. 17 illustrates another technique that may be used by the electrode system of FIG. 15 to attach the distal tip of the positioner to the electrode array at an attachment location near the distal tip of the electrode array;

FIG. 17A is a sectional view of the attachment technique shown in FIG. 17 as seen through the plane 17A—17A of FIG. 17;

FIGS. 21, 21A and 21B illustrate various views of the insertion tube.

Corresponding reference characters indicate corresponding components throughout the several views of the drawings.

DETAILED DESCRIPTION OF THE INVENTION

The following description is of the best mode presently contemplated for carrying out the invention. This description is not to be taken in a limiting sense, but is made merely for the purpose of describing the general principles of the invention. The scope of the invention should be determined with reference to the claims.

The invention described herein teaches one type of electrode system that may be used with a cochlear stimulation system. Other electrodes and electrode systems may also be used for this purpose as disclosed, e.g., in Applicant's previously-filed patent applications Ser. No. 09/140,033, filed Aug. 26, 1998, now U.S. Pat. No. 6,070,105; Ser. No. 09/140,035, filed Aug. 26, 1998; now U.S. Pat. No. 6,125,302; Ser. No. 09/247,734, filed Feb. 9, 1999, now U.S. Pat. No. 6,129,753; and Ser. No. 09/298,410, filed Apr. 23, 1999, now U.S. Pat. No. 6,195,586; all of which are incorporated herein by reference. The materials, dimensions, methods of manufacture, and the like, described in these referenced patents are also applicable to the present invention.

Figure 1A:
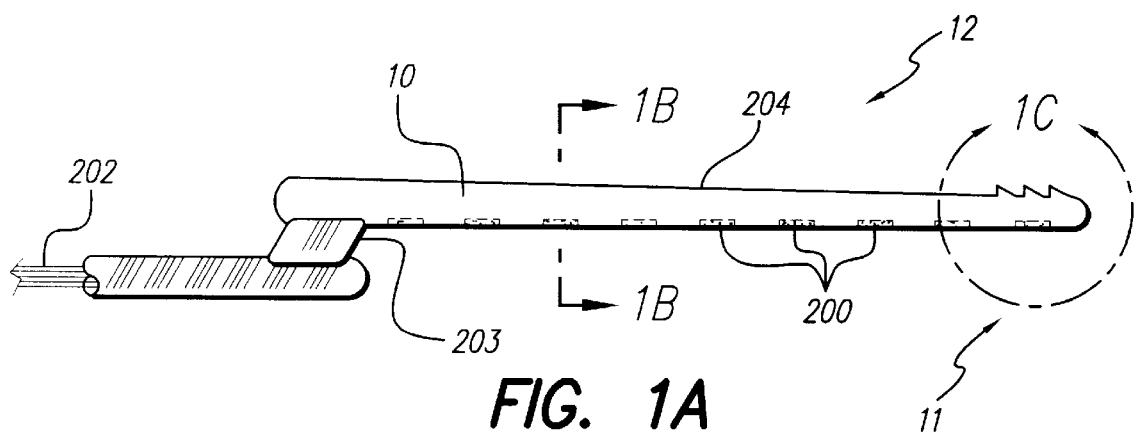
FIGS. 1A and 1B show a side and cross-sectional view, respectively, of one embodiment of an electrode array which may form part of the electrode system of the present invention.
Figure 1B:
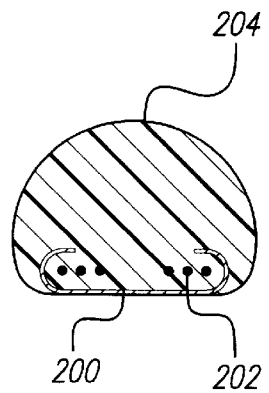

Turning first to FIGS. 1A and 1B, there is shown a side and a cross-sectional view, respectively, of an electrode array 10 that forms part of an electrode system 12 made in accordance with a first embodiment of the present invention. The cross-sectional view of FIG. 1B is taken along the line of 1B—1B of FIG. 1A. A distal end portion 11 of the array 10 is shown in FIG. 1C.

Figure 1C:
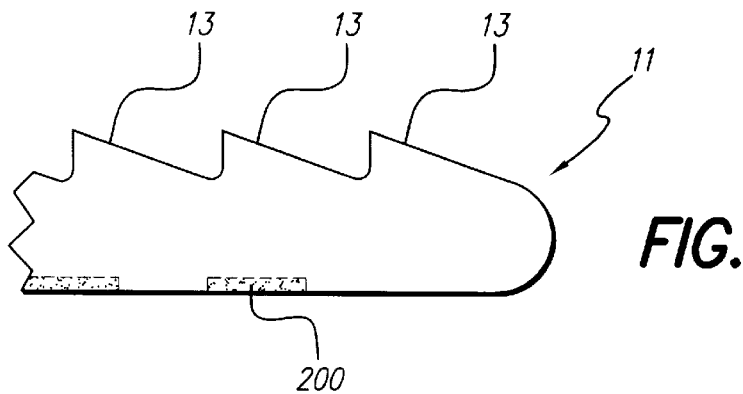
FIG. 1C illustrates an enlarged view of the engaging barbs used at a distal end of the electrode array shown in FIG. 1A.

As seen in FIGS. 1A, 1B and 1C, the electrode array 10 includes a plurality of spaced-apart electrode contacts 200, formed within or carried on a flexible carrier 204. Each of the electrodes is connected to at least one wire 202 which is embedded within the carrier 204. A proximal end of the these wires 202 (not shown) allows selective electrical connection to be made with each electrode contact 200 through use of a tissue stimulator, e.g., a cochlear stimulator. An offset portion 203, or bend, is formed in the carrier 204 to facilitate insertion of the electrode array 10 into the cochlea. Such offset 203, inter alia, not only identifies the side of the carrier 204 on which the electrodes 200 are located, but also serves as a physical stop that prevents insertion of the electrode array 10 into the scala tympani 102 of the cochlea 100 to a depth deeper than is desired. (Note, hereafter, the "electrode contacts 200" may be referred to simply as the "electrodes 200".)

As an important feature of the first embodiment of the invention, the distal end portion 11 of the electrode array 10 includes a plurality of engaging members, e.g., sloping barbs or teeth 13. These barbs 13, as explained below, help maintain the electrode array 10 in its desired position against the modiolus wall of the cochlea once it is inserted into the cochlea.

Figure 2A:
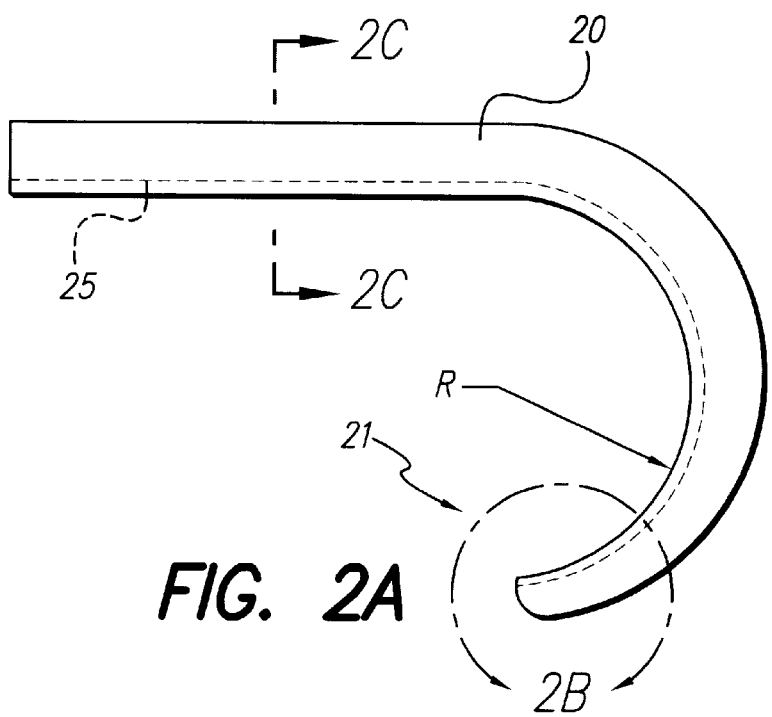
FIGS. 2A and 2C show a side and cross-sectional view, respectively, of a curved positioner that may also form part of the electrode system of the present invention.
Figure 2B:
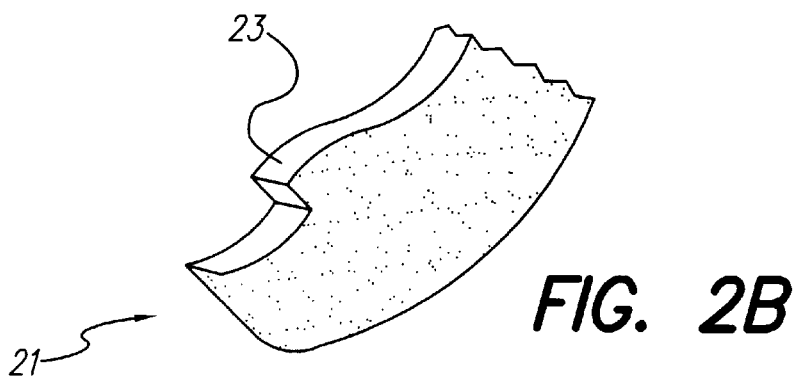
Figure 2C:
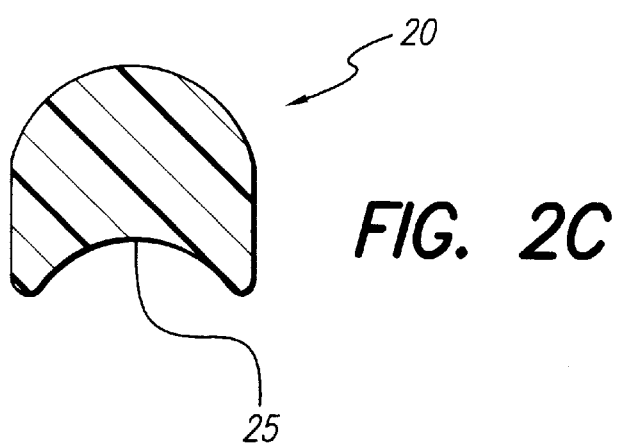

A second component of the electrode system of the first embodiment is a positioner 20, as illustrated in FIGS. 2A, 2B and 2C. FIG. 2A shows a side view of the positioner 20. FIG. 2B shows an enlarged view of a distal end portion 21 of the positioner 20, including a barb 23 or other suitable engaging member. Typically, the distal end of the positioner 20 will include a plurality of barbs 23, other engaging members, formed therein. FIG. 2C shows a cross-sectional view of the positioner 20 taken along the line 2C—2C of FIG. 2A. As seen in FIG. 2C, the positioner 20 typically includes a shallow smooth groove or channel 25 located along one side thereof. This channel or groove 25, as seen by the dotted-line representation of the bottom of the channel in FIG. 2A, traverses the entire length of the positioner 20. Such channel or groove 25 is not necessary for all embodiments of the positioner 20.

The flexible positioner 20 is preferably made from a silicone polymer, and may be molded to assume the curved shape shown in FIG. 2A, or it may be molded to assume a more straightened shape. If curved, the radius of curvature "R" is selected to be somewhat larger than the natural curvature of the cochlea. That is, when inserted into the cochlea, the positioner 20 will ideally a tighter wind or coil than that afforded by its formed curved shape. This assures that when inserted into the cochlea, the positioner 20 is held away from the modiolar wall 104, leaving a cavity or channel 22 (see FIG. 4B) against the modiolar wall. Such channel 22 provides a space wherein the electrode array 10 may be inserted.

Figure 3A:
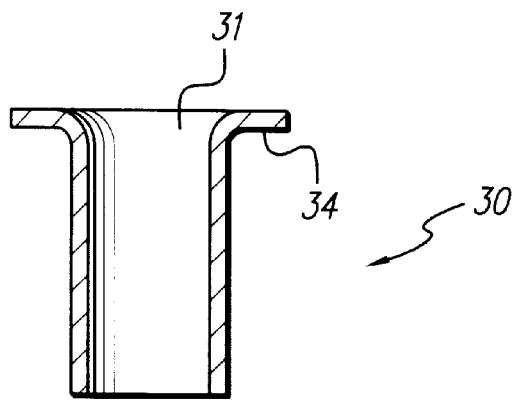
FIGS. 3A, 3B and 3C illustrate a cross-sectional, top, and perspective view, respectively, of an insert that forms part of the electrode system of the present invention, which insert is used to guide the electrode as it is inserted into the cochlea.
Figure 3B:
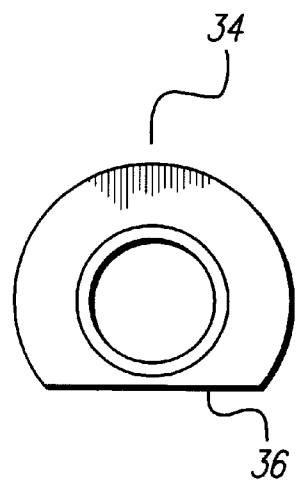
Figure 3C:
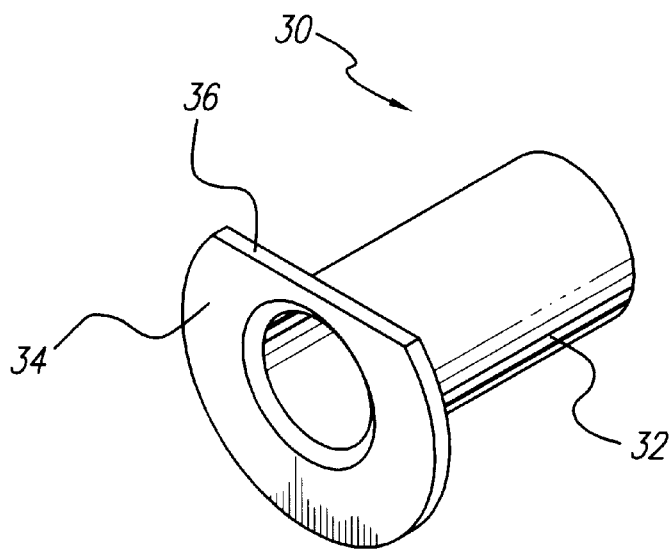
Figure 5:
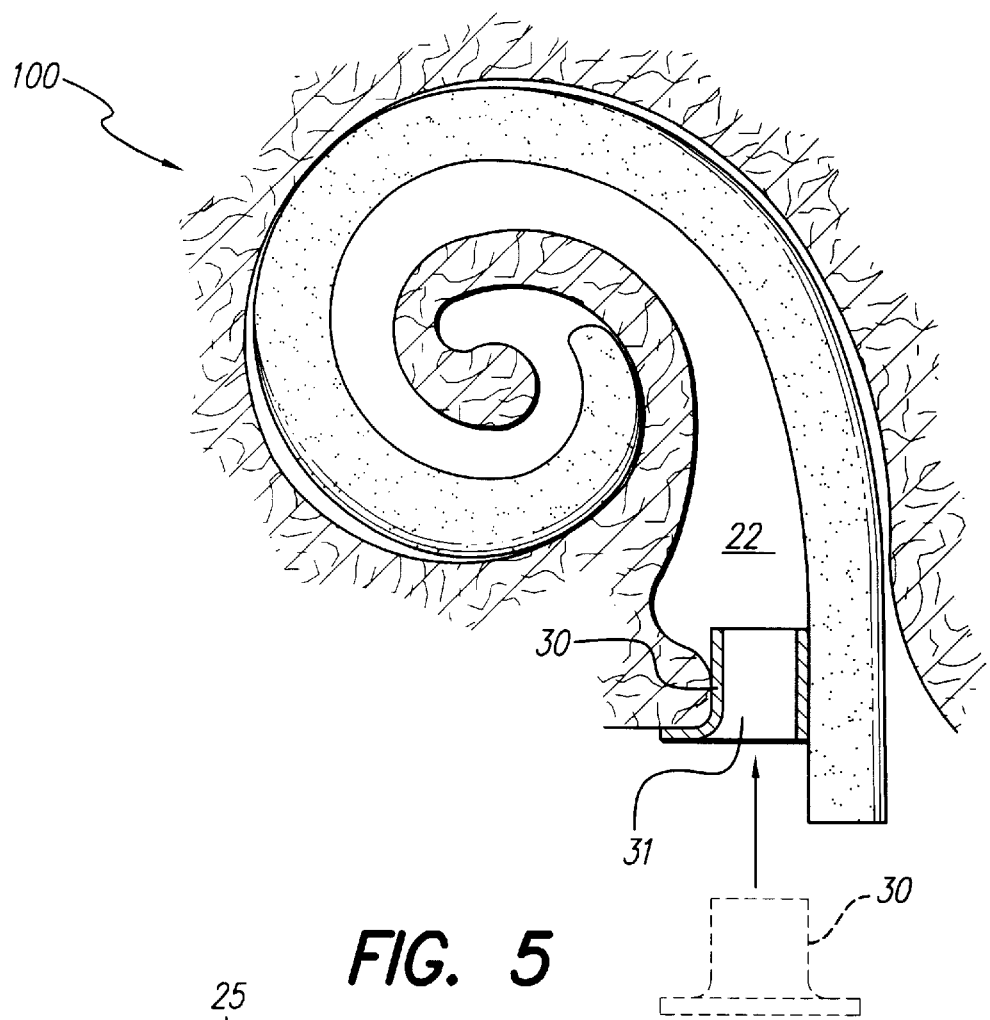
FIG. 5 shows a schematic representation of the spiraling scala tympani of the cochlea with the positioner inserted therein, and further illustrates the placement of an electrode-guiding insert into the front opening of the scala tympani.

A third component of the electrode system of the first embodiment, in accordance with at least one variation thereof, is an electrode-guide 30 as shown in FIGS. 3A, 3B and 3C. The guide 30 is designed to be inserted into the proximal end of the cavity or channel 22 formed between the modiolar wall and the positioner 20. The guide 30 includes a sleeve portion 32 and a flange portion 34. The sleeve portion 32 includes an opening or channel 31 therein having a size that allows the electrode array 10 (FIG. 1A, 1B) to readily slide therethrough. A portion of the flange 34, as seen best in FIG. 3B, is removed, thereby forming a straight edge 36 on one side of the flange. As will be evident from FIG. 5, below, this removed portion of the flange allows the insert 30 to fit snugly against the positioner 20 (i.e., the straight edge 36 fits up against the positioner 20) when the insert 30 is inserted into the cochlea.

The electrode-guiding insert 30 is made from a biocompatible material, such as platinum (Pt), titanium (Ti) or Teflon.

It is to be noted, as described more fully below, that the electrode-guiding insert 30 is optional, and may be omitted. Moreover, in other embodiments of the invention, as is also described more fully below, a guiding insert of the type shown in FIG. 3C, or similar guiding insert, may be used to help insert the positioner 20 into the cochlea after the electrode array 10 has first been inserted therein.

Figure 4A:
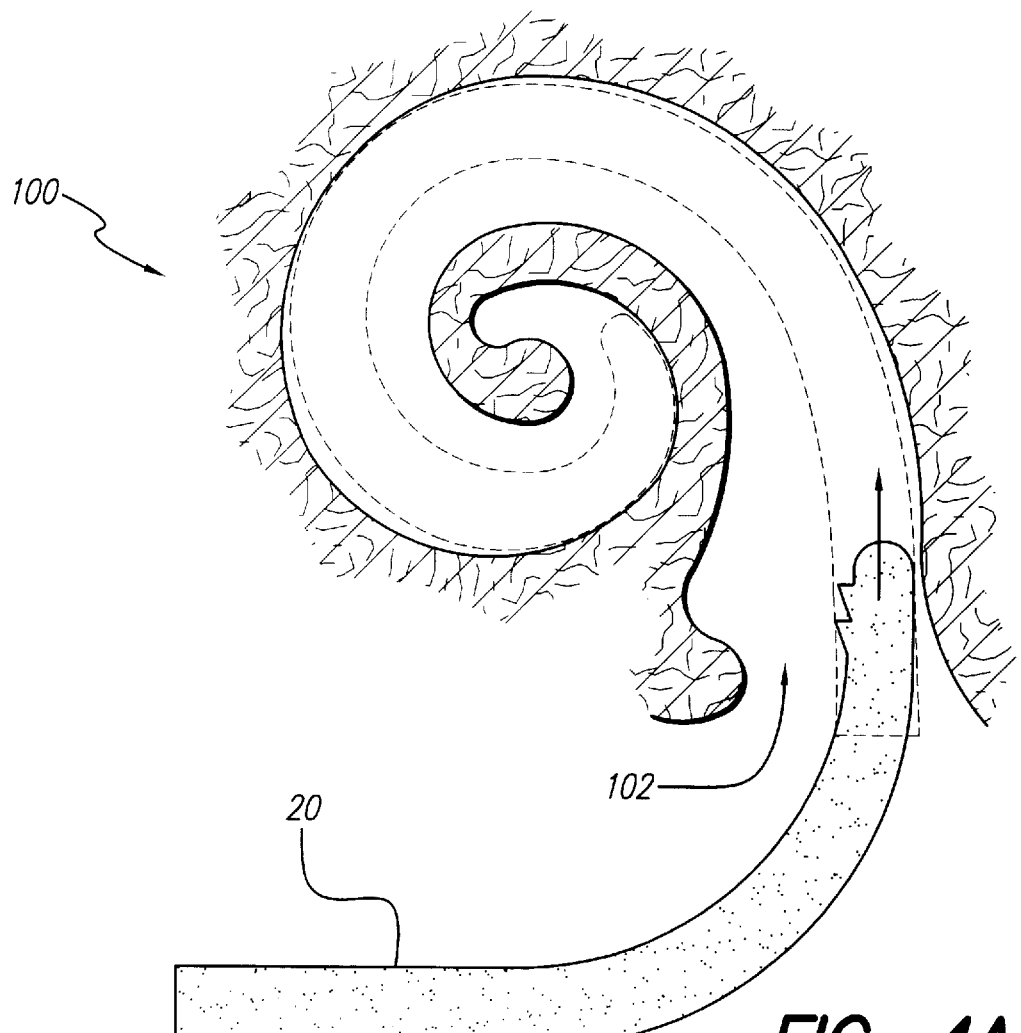
FIG. 4A illustrates insertion of the curved positioner into the scala tympani of the cochlea.
Figure 4B:
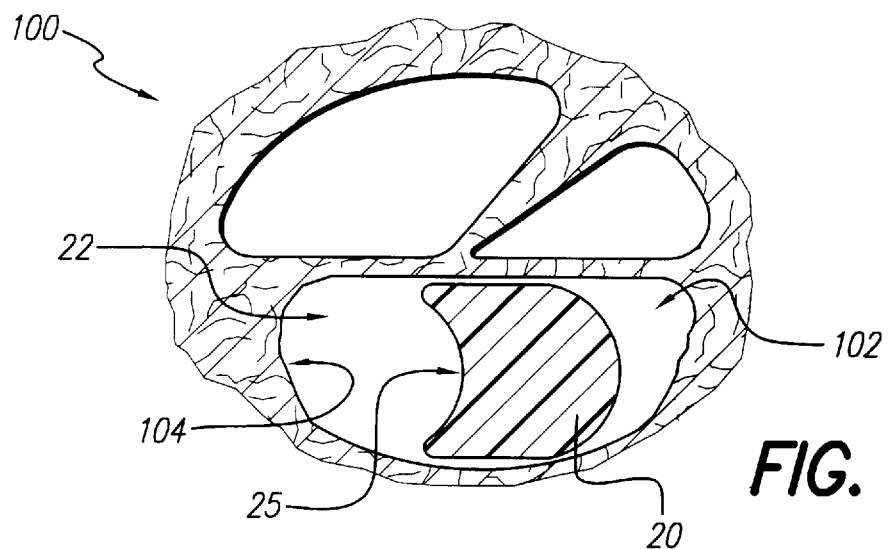
FIG. 4B shows a cross-sectional view of the cochlea with the positioner placed within the scala tympani.

Next, the method of using the electrode system of the first embodiment of the invention will be described in connection with FIGS. 4A through 6B. First, as shown in FIGS. 4A and 4B, the flexible positioner 20 is inserted into the scala tympani 102 (one of the channels of the cochlea 100) to the desired depth. The desired depth typically involves a rotation of about 360 degrees and causes, as seen best in FIG. 4B, the positioner 20 to rest against the outer or lateral wall of the scala tympani 102. This position leaves a channel or opening 22, one side of which is defined by the positioner 20, e.g., the groove 25 of the positioner 20, adjacent the inner wall (modiolus 104) of the scala tympani. The opening 22 is preferably slightly larger than the cross-section of the electrode array 10.

Advantageously, the super-flexible nature of the positioner 20 prevents it from causing damage to the cochlear structure. At the same time, once inserted, the positioner 20 provides a guide for the electrode array 10, and protects the cochlear walls from being damaged or touched directly by the stiffer electrode body 204.

Figure 6A:
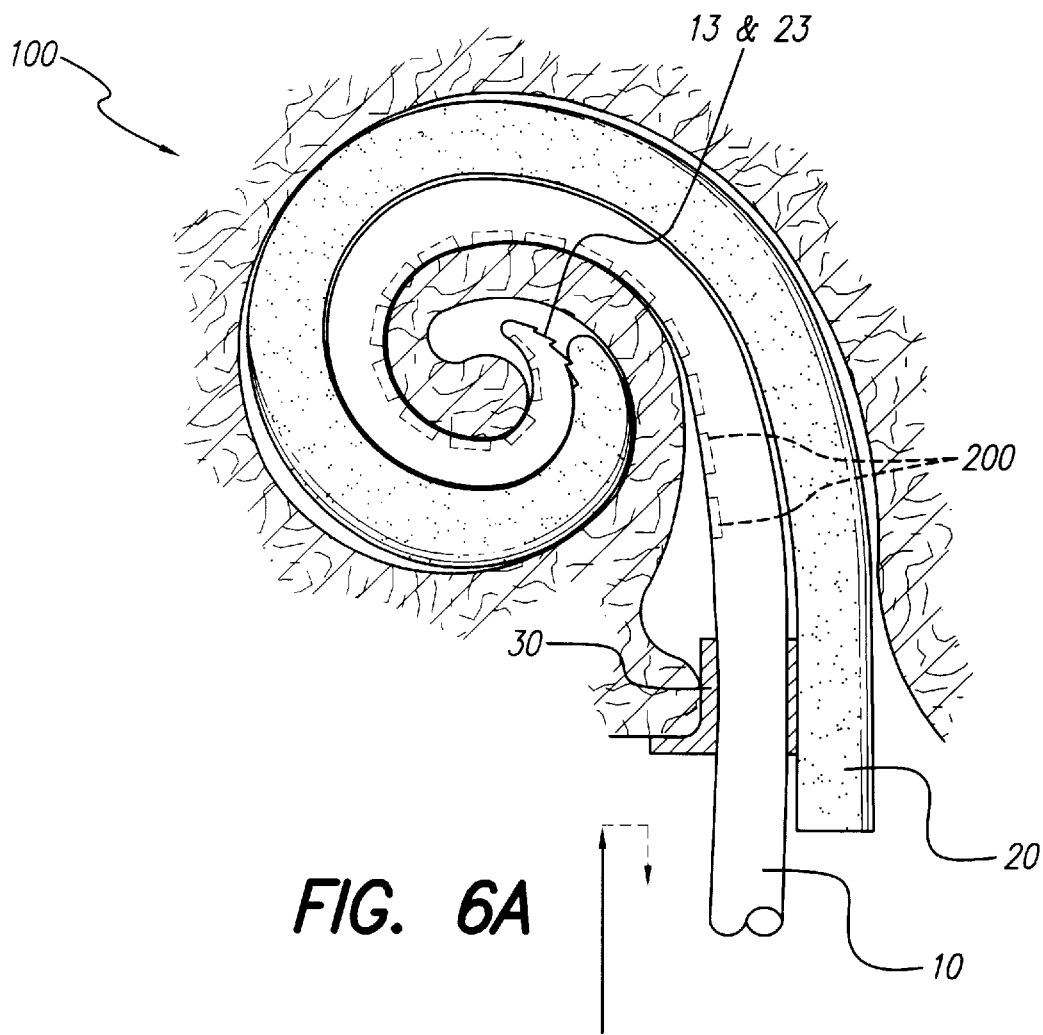
FIG. 6A is a schematic representation of the cochlea as in FIG. 5, but with the electrode array having been inserted into the scala tympani through the electrode-guiding insert.
Figure 6B:
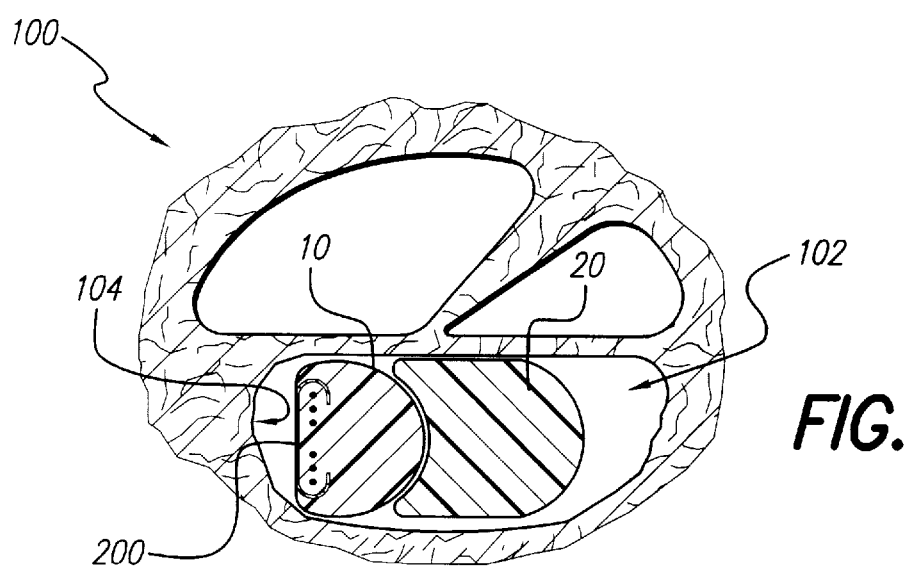
FIG. 6B is a cross-sectional view of the scala tympani of FIG. 6A, showing the manner in which the positioner forces the electrode array to hug the modiolus of the cochlea.

Once the positioner has been inserted to the desired depth, an electrode-guiding insert 30 (if used) is pushed into the opening of the channel 22. When this insertion is performed, the flat or straight side 36 of the flange 30 is placed against the grooved, or inner, side of the positioner 20, as seen best in FIG. 5. (The "inner" side of the positioner, regardless of whether the positioner has a groove or not, is that side on the inside of the curve of the positioner, i.e., that side facing the modiolar wall 104.) With the positioner 20 and electrode-guiding insert 30, in place, the electrode array 10 is next inserted through the opening 31 of the guiding insert 30 to the desired depth as shown in FIGS. 6A and 6B. Insertion is performed so that the electrodes 200 lie on the inside curve of the electrode array as it is inserted into the cochlea, thereby placing these electrodes 200 adjacent the modiolar wall 104.

The desired depth of insertion is preferably beyond the depth of the positioner 20. Advantageously, because the carrier body 204 of the electrode array 10 is tapered, having a smaller cross-sectional area at its distal tip than it does at its proximal end, it may be sized so that the diameter of the opening 31 within the guiding insert 30 effectively prevents further insertion once full insertion has occurred.

As explained above, the distal end portion 11 of the electrode array 10 includes engaging members, e.g., locking teeth or barbs 13, that engage with corresponding engaging members, e.g., teeth or barbs 23, located at the distal end of the positioner 20. Once the electrode array 10 has been inserted, the electrodes 200 are positioned very close to the modiolus of the cochlea, as desired. As a final optimization of the position of the electrode contacts 200 of the electrode array, the electrode array 10 may be pulled back slightly (about 2 mm). This backward motion assures that the distal end portions 11 and 21 of the electrode array 10 and the positioner 20 are engaged by the barbs 13 and 23 located thereon. Such engagement may further serve to force the electrode contacts 200 into close contact, e.g., direct contact, with the modiolar wall.

A preferred method of making the electrode array 10 is described in copending patent application Ser. No. 09/140,034, now U.S. Pat. No. 6,038,484, which patent is incorporated herein by reference. It is to be emphasized that the method disclosed in the referenced application is not the only way an electrode array suitable for use with the electrode system of the invention could be made. Rather, it merely represents an easy and inexpensive (and thus a preferred) way in which the electrode array may be fashioned.

Alternative Embodiments

Figure 9E:
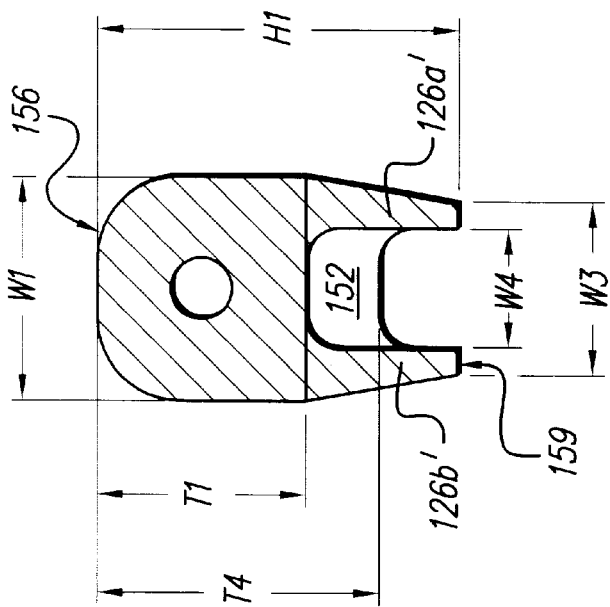
FIG. 9A is a side section view, rotated 90° from the view shown in FIG. 8A, of the proximal end of the positioner of FIG. 7.
FIG. 9B is a side section view, rotated 90° from the view shown in FIG. 8B, of the distal end of the positioner of FIG. 7.
FIG. 9C is a sectional view of the positioner of FIG. 9B taken near the middle of the positioner along the line 9C—9C.

Other embodiments of the invention may also be used. For example, FIGS. 7, 8A–8B, and 9A–9E, depict an alternative embodiment of a positioner 150 that may be used with the invention. Whereas the positioner 20 described previously in connection with the first embodiment of the invention naturally assumes a curved shape, e.g., a shallow hook shape, the positioner 150 shown in FIGS. 7, 8A–8B and 9A–9E, is formed to assume a naturally straight shape. In FIGS. 7, 8A–8B and 9A–9E, FIG. 7 shows a broken perspective view of the distal and proximal ends of the positioner 150; FIGS. 8A and 8B show a bottom view of the proximal and distal ends of the positioner, respectively, looking into the electrode channel created by the proximal side walls and distal keeper tabs; FIGS. 9A and 9B show a side view of the proximal and distal ends of the positioner 150, respectively; and FIGS. 9C, 9D and 9E are sectional views taken along the lines 9C—9C, 9D—9D, and 9E—9E in FIGS. 9A and 9B. Representative dimensions (expressed in millimeters) of the positioner 150 are specified throughout the specification. It is to be understood, however, that these dimensions are only representative of typical dimensions that may be used during the manufacture of the positioner 150, and are not intended to be limiting, except to the extent that such dimensions are present in the claims.

It should also be understood that the positioner 150 may be made from any suitable biocompatible material using techniques known in the art. Typically, the positioner 150 will be made using conventional molding techniques from a silicone polymer. A suitable silicone polymer is commercially available under the name LSR-25 or LSR-70, which vary in degree of softness and flexibility, where LSR-70 is not as soft nor as flexible as LSR-25.

Figure 7:
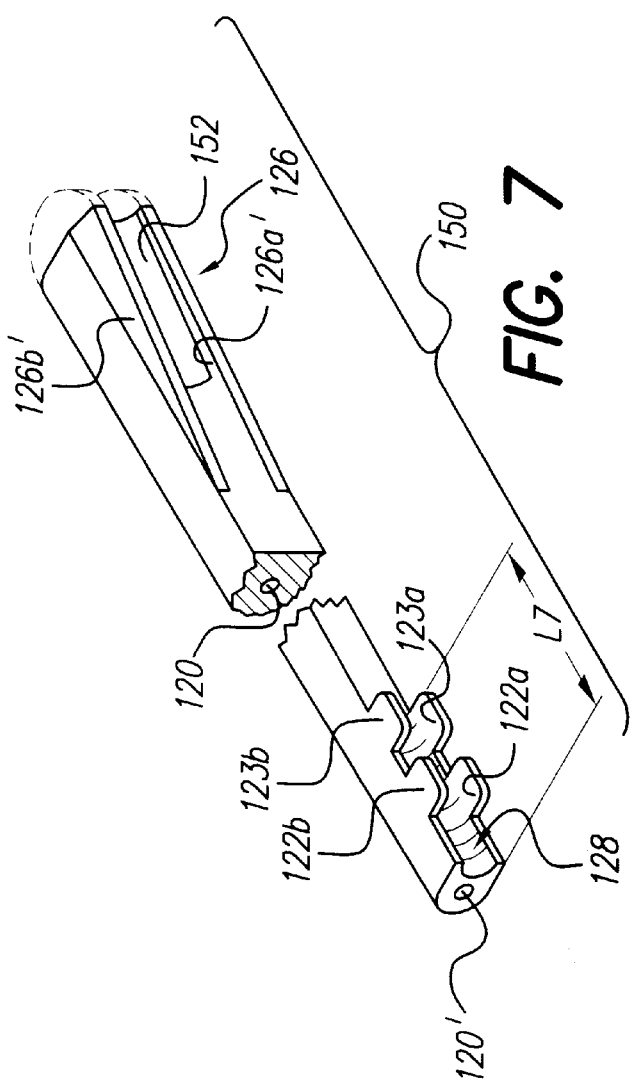
FIG. 7 shows the proximal and distal end regions of yet a further embodiment of a positioner that may be used with the invention.

As seen in FIGS. 7, 8A–8B and 9A–9E, the positioner 150 is formed from a suitable silicone polymer in a relatively straight shape, forming an elongate flexible member. The entire positioner is best seen in FIG. 7. Such flexible member has a distal tip and a proximal end. A first pair of keeper tabs 122, comprising tabs 122a and 122b (sometimes referred to as "keeper wings", or just "wings"), protrude from the positioner in the vicinity of its distal tip. A first tab 122a of the first pair of tabs 122 is adapted to lie against one side of the electrode array near the distal end of the array. The other tab 122b of the first pair of keep tabs 122 is similarly adapted to lie against an opposite side of the electrode array. The space between the tabs 122a and 122b thus defines a distal channel wherein the distal end of the electrode array may be placed. This distal channel keeps the distal end of the positioner 150 alongside the distal end of the electrode array when the positioner 150 inserted into the cochlea alongside the electrode array.

A second pair of keeper tabs 123, comprising tabs 123a and 123b (sometimes also referred to as "keeper wings", or just "wings"), protrude from the positioner at a location that is near the location where the first pair of keeper tabs 122 protrude, but closer to the proximal end of the positioner 150. A first tab 123a of the second pair of tabs 123 is adapted to lie against one side of the electrode array, and the other tab 123b of the second pair of keeper tabs 123 is similarly adapted to lie against an opposite side of the electrode array. The space between the tabs 123a and 123b thus further defines the distal channel wherein the distal end of the electrode array may be placed.

In one embodiment, a space, L9, where L9 is at least 0.5 mm separates a proximal edge of the keeper tab 122*a* or 122*b* from a distal edge of the keeper tab 123*a* or 123*b*, as depicted in FIG. 9B.

The first pair of keeper tabs 122, as well as the second pair of keeper tabs 123, are formed of the same material as the elongate flexible member that makes up the positioner 150. As a result, the keeper tab pairs 122 and 123 are also flexible, forming an integral part of the flexible member that makes up the positioner.

The positioner 150 further includes a pair of side walls 126 protruding from a proximal end of the positioner. One side wall 126*a*' of the pair of side walls 126 is adapted to lie against one side of the proximal end of the electrode array, and the other side wall 126*b*' of the pair of side walls 126 is adapted to lie against an opposite side of the proximal end of the electrode array. The space between the side walls 126*a*' and 126*b*' thus defines a proximal channel adapted to receive a corresponding proximal end of the electrode array. This proximal channel is adapted to keep the proximal end of the positioner alongside the proximal end of the electrode array when the positioner 150 is inserted into the cochlea alongside, i.e., along the back side of, the electrode array.

A lumen or passageway 120 is formed to pass longitudinally through the body of the positioner 150. This lumen or passageway 120 is closed at the distal end of the positioner. A marker, i.e., a metal ball, may be inserted into the closed end of the passageway 120 of the positioner 150 to facilitate viewing the location of the distal tip of the positioner with an imaging system, e.g., an X-ray system. During insertion, the lumen or passageway 120 is adapted to receive a stylet wire. The stylet wire is used as part of a tool during the insertion process to facilitate insertion of the positioner 150 into the scala tympani of the cochlea after the electrode array has already been inserted therein.

Included within the distal channel formed between the first and second pair of keeper tabs 122 and 123 of the positioner are engagement members 128. These engagement members 128, in one embodiment, comprise slanting teeth. These slanting teeth are adapted to engage with the serrations, or equivalent protruding or engageable members, on the back side of the electrode array when the positioner 150 is inserted into the cochlea alongside the electrode array, as taught in Applicant's copending patent application, Ser. No. 09/443,627,filed Nov. 19, 1999, which application is incorporated herein by reference. As such engagement occurs, pushing the positioner 150 deeper into the cochlea also carries the electrode array deeper into the cochlea. Advantageously, however, the positioner 150 may be pulled backward within, or even entirely removed from, the cochlea while still leaving the electrode array deeply inserted within the cochlea. Thus, it is seen that the electrode system provided by this embodiment of the invention advantageously allows the flexible positioner 150 to be detachably engaged with the distal region of the electrode array during insertion, but which positioner 150 is easily separated, and detached from, the electrode array should the need arise to remove the positioner 150 from the cochlea.

The positioner 150 has a sloping floor 152 in the bottom of the electrode channel located between the side walls 126 at the proximal end of the positioner. That is, as seen best in FIGS. 7 and 9A, the pair of proximal side walls 126, comprising a right side wall 126*a*' and a left side wall 126*b*' (as viewed in FIG. 9E), have a varying height that, when viewed in the side view of FIG. 9A causes an upper edge of each side wall to slope from a maximum height at the extreme proximal end of the positioner (at sectional line 9E—9E in FIG. 9A) to a zero height, or near zero height, at a distal most location, shown in FIG. 9A as point 154. The length of the side walls, for the embodiment shown in FIG. 9A, from the sectional line 9E—9E to the point 154 is, L5, where L5 is approximately 7.0 mm. The maximum height (H1) of the side walls, as seen best in FIG. 9E, and as measured from a top side 156 of the positioner is about 1.70 mm.

The overall thickness, T1, of the positioner 150 at the proximal end of the positioner, i.e., at the sectional line 9E—9E, as measured from the top side 156 of the positioner to a bottom side 157 of the positioner, as best seen in FIG. 9E is approximately 0.90 mm. This thickness narrows towards the distal end of the positioner, as seen best in the sectional views of FIGS. 9C and 9D. That is, as seen in FIG. 9D, the thickness, T2, of the positioner at the distal end of the positioner, i.e., at sectional line 9D—9D, is approximately 0.5 mm; whereas as seen in FIG. 9C, the thickness, T3, of the positioner near the mid-point of the positioner, i.e., at sectional line 9C—9C, is approximately 0.6 mm. Thus, it is seen that the thickness of the positioner tapers from approximately 0.90 mm at its proximal end to about 0.5 mm at its distal end.

The width of the positioner, as measured from its left side to its right side also tapers, as evident from FIG. 9E (proximal end) and FIG. 9D (distal end) from, W1, where W1 is approximately 1.10 mm at the proximal end to about, W2, where W2 is about 0.70 mm at the distal end.

As illustrated best in FIGS. 7, 9A and 9E, the channel formed between the side walls 126*a*' and 126*b*' has a sloping floor 152 therein. At the proximal end of the positioner 150, i.e., at the sectional line 9E—9E, the floor 152 is spaced a distance T4, where T4 is approximately 1.30 mm from the top side 156 of the positioner. This floor, for the embodiment shown in FIGS. 7, 9A, and 9e, linearly slopes down to the bottom side 157 of the positioner at a point 158, located a distance L6, where L6 is about 3.0 mm distally from the sectional line 9E—9e (see FIG. 9A). The function of the floor 152 is to assure that the electrode array, when placed into the proximal channel located between the side walls 126, is nudged or positioned against the modiolar wall of the cochlea more than it would be without the floor, thereby helping to maintain modiolar-wall contact, or near contact, at the basal end of the scala tympani (near the round window). The floor 152 also functions as a soft wedge to help firmly maintain the positioner and electrode array in their desired positions within the scala tympani.

As further seen best in FIGS. 8A and 9E, the side walls 126 of the positioner 150 have exterior walls that are thicker near the bottom 157 of the positioner 150 than they are at a top edge 159. That is, as seen in FIG. 9E, the width, W1, of the positioner is about 1.10 mm at the proximal end (at section line 9E—9E) of the positioner, and this also is the distance between the exterior edges of the side walls 126 at a base of the side walls (i.e., at point 157). At the top edge 159 of the side walls, however, the distance, W3, between the exterior edges of the side walls 126 narrows to about 0.85 mm. The distance, W4, between the interior walls of the side walls 126, however, does not change from the base to the top, this distance remaining at about 0.60 mm.

FIG. 7 shows the engaging members 128 of the positioner 150 to spread over a distance L7 that extends from the extreme distal tip of the positioner 150 through second pair of keeper tabs 123. Alternatively, as seen in FIG. 8B, the engaging members 128 may be dispersed over a smaller distance L8 that does not extend all the way to the distal tip.

FIG. 7 also shows the hole or passageway 120 that passes through the positioner 150. During manufacture, the hole or passageway 120 will typically pass all the way through the positioner to the distal end of the positioner, where it is shown as hole 120'. At the distal end, the hole 120' is typically plugged with a suitable material, e.g., LSR 25, so that a stylet wire, when inserted into the passageway 120, will not exit through the distal end of the positioner.

The engagement members 128 are typically slanting teeth or ridges as previously described. However, any suitable engaging member 128 may be used that is adapted to engage with corresponding or mating engagement members positioned on the electrode array as the positioner 150 is inserted into the scala tympani after the electrode array has been inserted therein.

Figure 10:
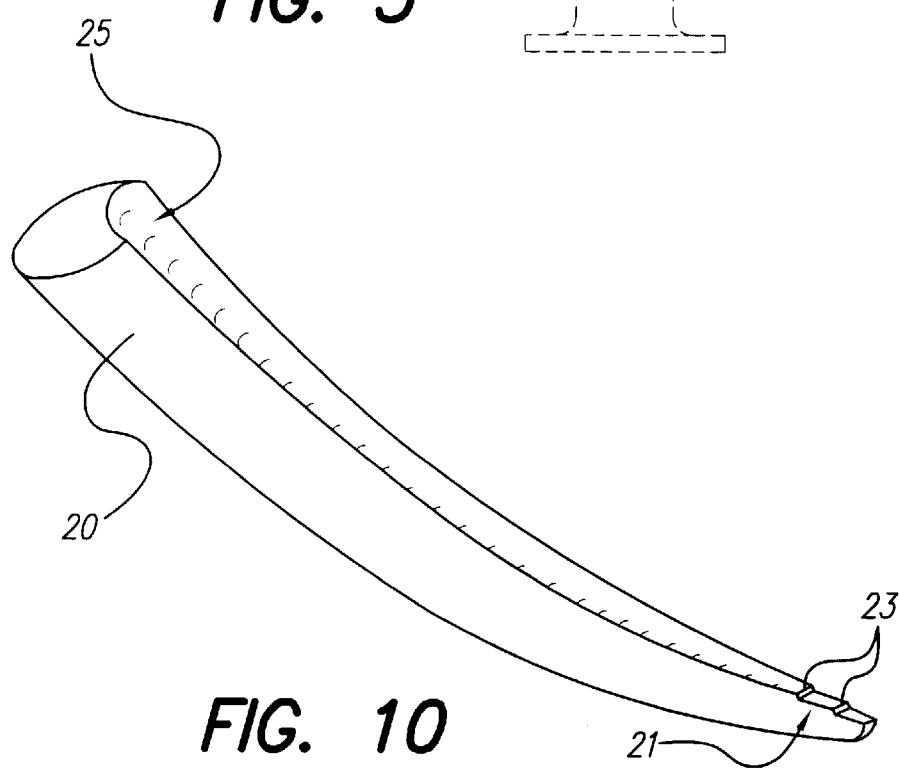
FIG. 10 is a perspective view of yet another embodiment of a positioner that may be made in accordance with the present invention, lying in a somewhat straightened position.

In yet another embodiment of the invention, the positioner 20 assumes a somewhat straightened position, but not as straight as in FIGS. 7, 8A–8D and 9A–9E, and yet not as curved as in FIG. 2A. Such an intermediate curved embodiment is shown in FIG. 10. The positioner 20 shown in FIG. 10 may be used with any type of electrode system or electrode array in order to help position the electrode contacts of the array in a desired position within the cochlea. When so used, the positioner may be inserted into the cochlea first (i.e., before insertion of the electrode array), as described above in connection with FIGS. 4A and 4B, or second (i.e., after insertion of the electrode array), as described more fully below.

Typically, as indicated above, the positioner 20 is curved, although the degree and amount of curvature is not critical given the flexible nature of the positioner. The distal end of the positioner 20 may include a plurality of barbs or bumps 23 formed therein. Moreover, the positioner 20 may include a smooth groove or channel 25 located along one side thereof to facilitate holding the electrode array 10 on that side of the positioner facing the modiolar wall. This channel or groove 25, when used, traverses the entire length of the positioner 20, or at least the length of the positioner up to the distal tip where the barbs or bumps 23 may be located.

As described above, the flexible positioner 20 is preferably made from a silicone polymer, and is molded to assume a generally curved shape, with a width or cross-sectional area that is tapered, as required, to match the cross-sectional area or width of the scala tympani of the cochlea. Preferably, the radius of curvature "R" of the positioner 20 is selected to be somewhat larger than the natural curvature of the scala tympani of the cochlea. That is, when inserted into the scala tympani, the positioner 20 ideally assumes a tighter wind or coil than that afforded by its formed curved shape. This assures that when inserted into the scala tympani, the positioner 20 is held away from the modiolar wall 104, leaving a cavity or channel 22 against the modiolar wall 104 wherein the electrode array 10, 10' or 10", or any other type of electrode array, may be inserted. Further, this preferred shape and positioning of the positioner within the cochlea improve the directional stability of the electrode array during insertion, i.e., help prevent rotation of the electrode array, thereby assuring that the electrode contacts remain positioned adjacent the modiolar wall.

Figure 11:
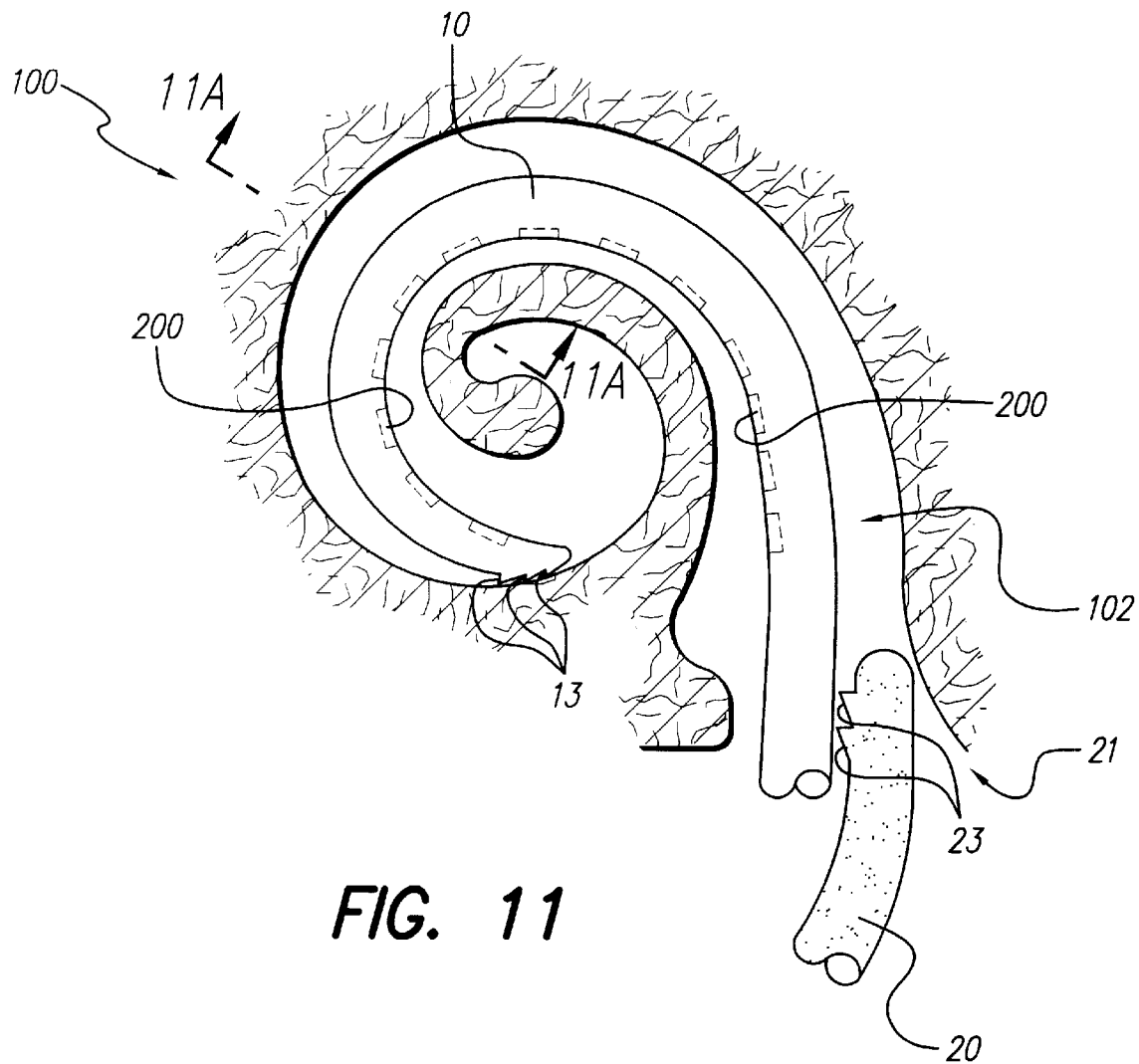
FIG. 11 is a schematic representation of the cochlea showing an alternate technique for insertion of the electrode array, and in particular showing the electrode array first inserted into the cochlea and showing the positioner inserted second into the cochlea.

One technique for inserting an electrode array 10 into the cochlea without having to use a guiding insert 30 is to first insert the electrode array 10 into the cochlea using any desired technique, as shown in the FIG. 11. Typically, during such insertion, the electrode contacts 200 of the electrode array 10 will be oriented to face the desired wall within the cochlea, e.g., the modiolar wall 104.

Figure 11A:
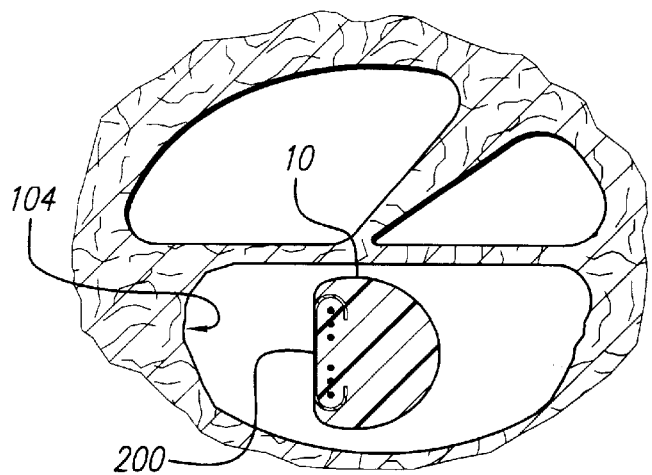
FIG. 11A is a sectional view taken along the line 11A—11A of FIG. 11.

As evident from the schematic representation of FIG. 11, as well as the sectional view of FIG. 11A, the electrode contacts 200 of the electrode array 10, when the electrode array 10 is first inserted into the cochlea are not held up against the inner wall (modiolar wall 104) of the cochlea 100. In order to position or hold the electrode contacts 200 up against the modiolar wall 104, the positioner 20 is also inserted into the cochlea, behind and alongside the electrode array 10, i.e., on the side of the electrode array 10 farthest from the modiolar wall 104, as seen in FIG. 11 (which shows the distal tip 21 of the positioner 20 just as it is first inserted behind the electrode array 10 within the cochlea).

Figure 12:
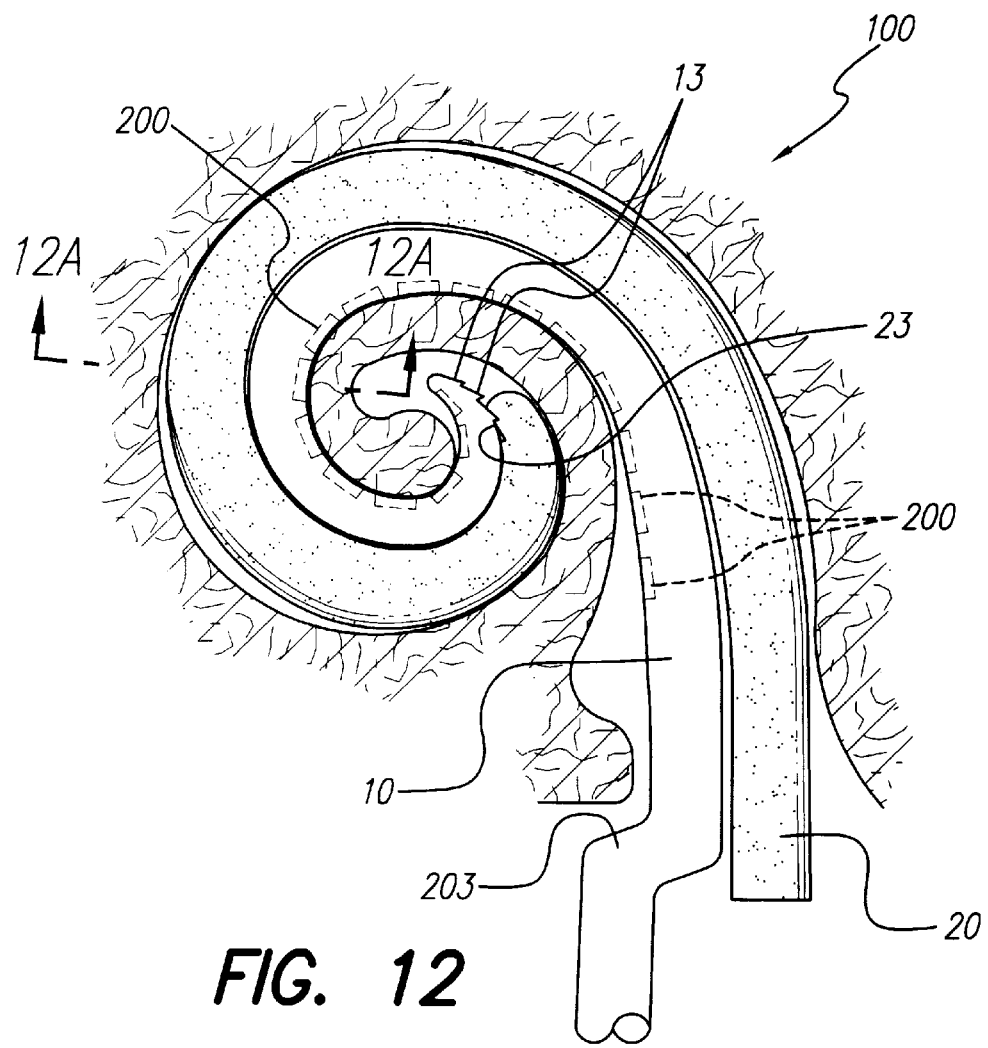
FIG. 12 is a schematic representation of the cochlea as in FIG. 11, but showing the positioner fully inserted into the cochlea.
Figure 12A:
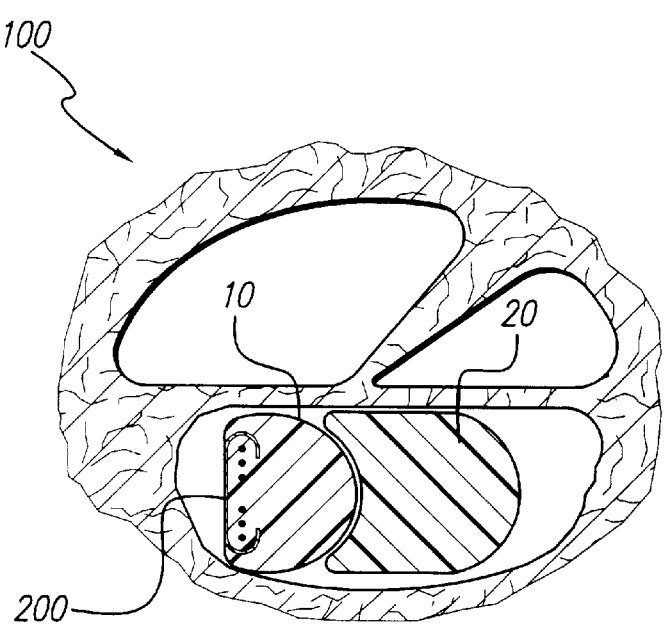
FIG. 12A is a sectional view of the cochlea taken along the line 12A—12A of FIG. 12.

As the positioner is pushed deeper into the cochlea, it forces the electrode array 10 up against the modiolar wall 104, which action causes most, if not all, of the electrode contacts 200 to be in direct or nearly direct contact (touching) the modiolar wall 104. Moreover, as the positioner 20 is pushed still deeper into the cochlea, it eventually grabs or engages with (either through a friction fit, and/or with the assistance of the barbs or bumps 23) the electrode array 10 and carries the electrode array 10 with it deeper into the cochlea, causing the electrode array 10 to be inserted, e.g., an additional ½ turn deeper into the cochlea than when initially inserted. Advantageously, once in such fully inserted position, as shown in FIGS. 12 and 12A, the barbs or bumps 23 on the positioner, in combination with the barbs, teeth or other engaging members 13 on the electrode array, prevent the electrode array 10 from sliding backwards out of the cochlea, yet allow the positioner, if needed, to be removed from the cochlea.

Note, typically the electrode array 10, as seen best in FIG. 1A, has an offset 203 located near its proximal end. Such offset 203 functions as a stop to prevent the electrode array from being inserted too deep into the cochlea. Even when such offset cannot effectively function as a stop, it can always function as a mark, to aid the physician to know when the desired insertion depth has been achieved, and also to know in which direction the electrode contacts are facing.

Turning next to FIGS. 13, 14, 14A, 14B and 14C, a further embodiment of a positioner 160 is illustrated. In most respects, the positioner shown in FIGS. 13, 14, 14A, 14B and 14C is the same as that described previously, and like reference numerals are used to described like components or elements. Hence, only the differences between the positioner 160 and the positioner 150 will be described. FIG. 13 is a broken bottom view of the positioner 160, showing its proximal and distal end regions. FIG. 14 is a side sectional view of positioner 160 taken along a longitudinal center line 172 of FIG. 13; and FIGS. 14A, 14B and 14C are sectional views taken along the sectional lines 14A—14A, 14B—14B, and 14C–14C, respectively, of FIG. 14.

One difference between the positioner 160 and the positioner 150 is the use of a platinum marker element 170 that is placed within the passageway 120 near the distal end of the positioner. Such marker 170 allows the location of the distal tip of the positioner to be easily detected using conventional imaging equipment, e.g., an X-ray machine. The passageway 120 is plugged with a suitable substance, such as LSR-25, at the distal end of the positioner.

Another difference between the positioner 160 and the positioner 150 is that the first pair of keeper tabs 122 used with the positioner 160 are located right at the distal tip of the positioner, rather than spaced back from the distal tip a small distance.

Yet another difference between the positioner 160 and the positioner 150 is that the engagement members 128 used with the positioner 160 are only placed in the region between the keeper tabs 122 and 123, rather than dispersed over a distance L7 or L8, as with the positioner 150.

A further difference between the positioner 160 and the positioner 150 is that the proximal side walls 126 used with the positioner 160 are straight. That is, as seen best in FIG. 14C, a right side wall 126a" and a left side wall 126b" have exterior and interior surfaces that are straight, and the thickness of these walls does not narrow, as is the case as is the case of the side walls 126a' and 126b' used with the positioner 150.

An additional difference between the positioner 160 and the positioner 150 is that a floor 152' of the positioner 160, between the side walls 126a" and 126b", slopes at a relatively steep angle, α, e.g., a 45° angle as shown in FIG. 14, beginning at a point 158' that is only about 2.0 mm from the proximal end (section line 14C—14C).

Figure 15:
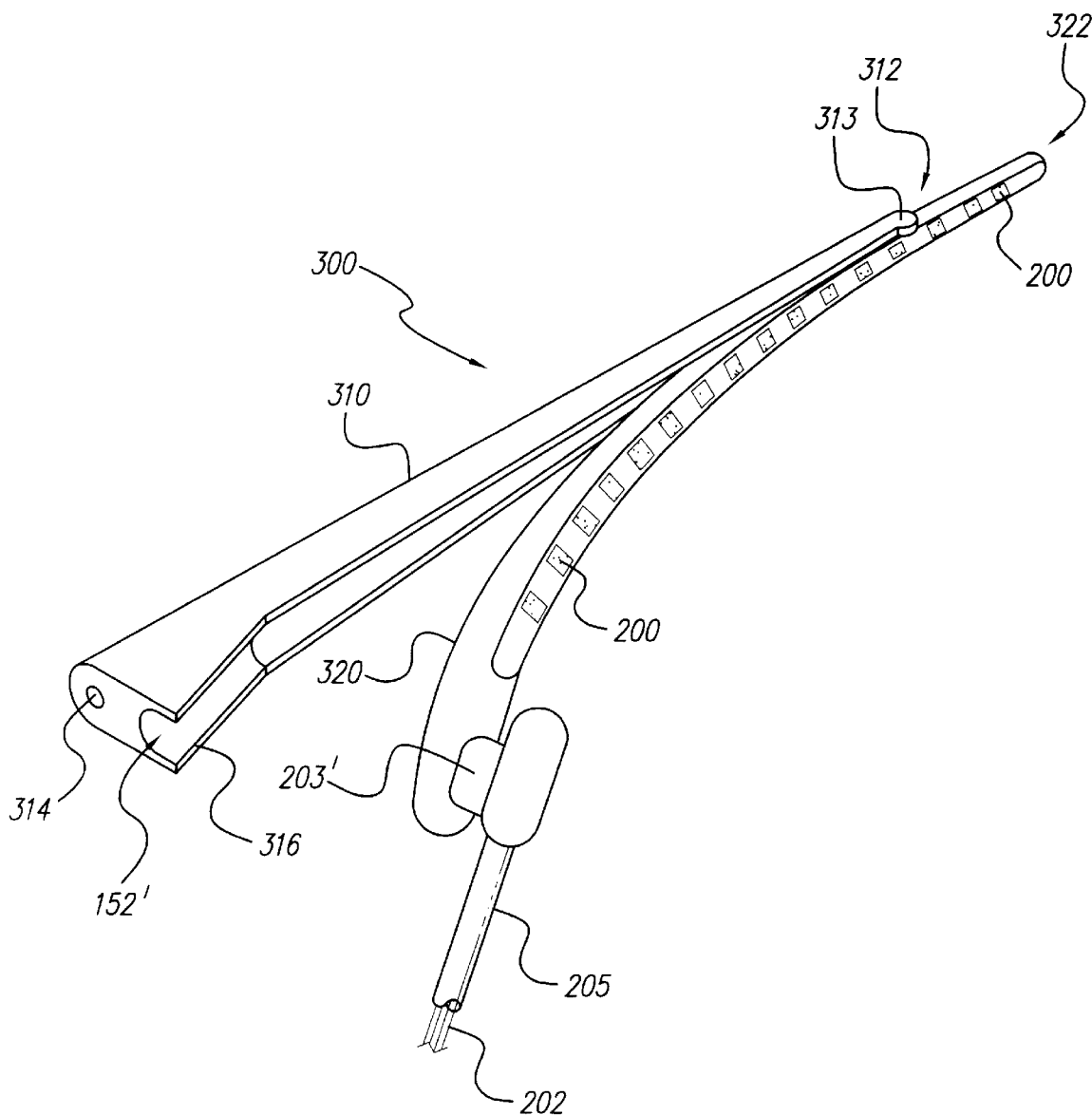
FIG. 15 is a perspective view of an embodiment of the electrode system of the present invention wherein the positioner is attached near the distal end of the electrode array.

Turning next to FIG. 15, a further embodiment of an electrode system 300 made in accordance with the invention is shown. The electrode system 300 includes an electrode array 320 and a positioner 310. Unlike prior embodiments, however, where the electrode array and positioner are separate detached elements, the positioner 310 of the electrode system 300 has its distal end 312 attached in some manner to the electrode array 320 at a point near, but not at, the distal tip of the electrode array. The electrode array 320 may be an electrode array substantially the same as previously described, e.g., substantially the same as the electrode 10 described in FIG. 1A and 1B, or as described in the referenced patent applications (see, e.g., U.S. patent application Ser. No. 09/247,734, filed Feb. 9, 1999, now U.S. Pat. i No. 6,129,753, incorporated herein by reference). In a preferred embodiment, the electrode array 320 includes a plurality of spaced-apart electrode contacts 200 along one side of a flexible carrier. The side on which the electrode contacts are located, or the side on which at least a portion of each electrode is exposed, is the side adapted to face the modiolar wall 104 of the cochlea. Wires 202, carried within the carrier of the electrode array, make electrical contact with various ones of the electrode contacts 200. An offset 203', near a proximal end of the electrode array 320, functions as a stop that prevents the electrode array from being inserted too deep into the cochlea, and further identifies the front side of the electrode array, i.e., identifies the side of the electrode array on which the electrode contacts 200 are exposed. A lead 205 extends from the offset 203' and carries the wires 202 (which are encased within the lead 205) to a suitable proximal connector (not shown) or other destination where the wires 202 are connected to appropriate electrical circuitry (not shown).

The positioner 310 may also be substantially the same as previously described, e.g., substantially the same as the positioner 150 described in connection with FIGS. 7, 8A, 8B, 9A–9E, or substantially the same as the positioner 160 described in connection with FIGS. 13, 14, 14A–14C. The main difference between the positioner 310 and the positioners 150 or 160 is that the positioner 310 is attached at its distal tip 312 to the electrode array 320. The point of attachment, i.e., the location where the distal tip 312 of the positioner 310 attaches to the electrode array 320, is about 3–5 mm from the distal end 322 of the electrode array. For the spacing of the electrode contacts 200 of an electrode of the type disclosed in the referenced Ser. No. 09/247,734 patent application, this distance corresponds to a location that is about 3 or 4 contacts from the distal end 322 of the electrode array.

The way in which the distal tip 312 of the positioner 310 is attached to the electrode array 320 near its distal end 322 varies. That is, the manner of attachment is not as important as the fact that an attachment of some kind be employed so that the positioner remains attached to the electrode array during and the insertion process.

Figure 16A:
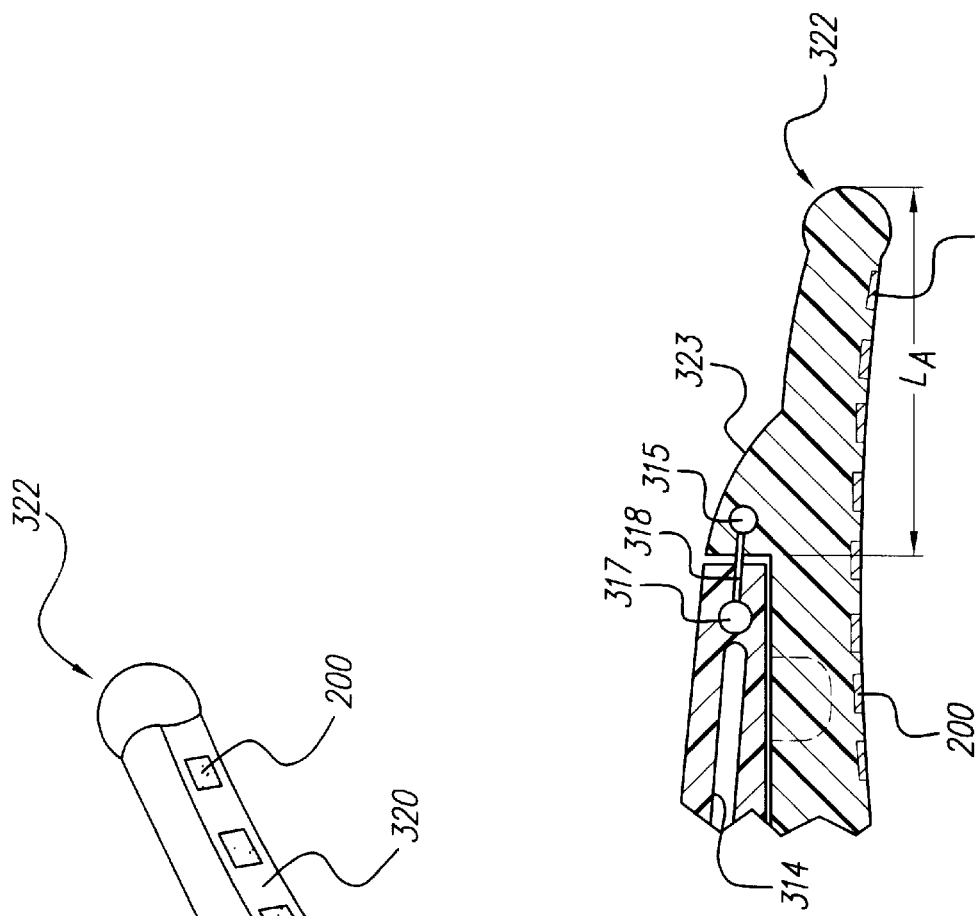
FIG. 16A is a longitudinal sectional view of the attachment technique shown in FIG. 16.
Figure 16:
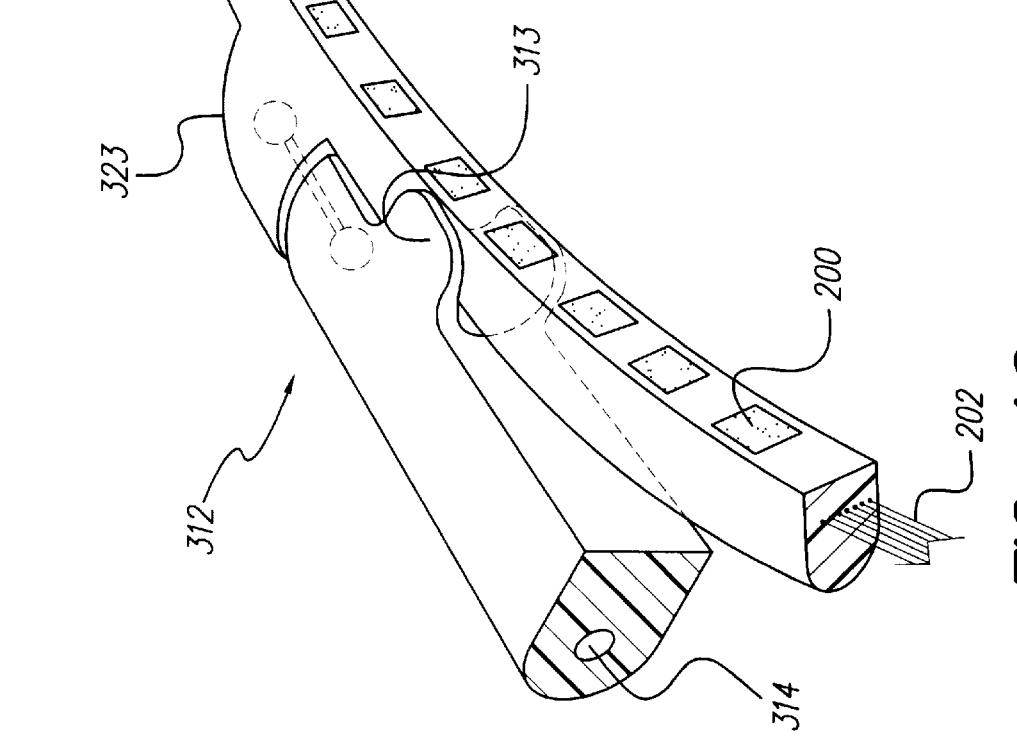
FIG. 16 illustrates one technique that may be used by the electrode system of FIG. 15 to attach the distal tip of the positioner to the electrode array at an attachment location near the distal tip of the electrode array.

One way in which the attachment may be carried out is depicted in FIGS. 16 and 16A. A hump 323 is formed on the back side (the side opposite the electrode contacts 200) of the electrode array 320. The distal tip 312 of the positioner 310 abuts against a proximally-facing side of the hump 323. A ball 315 is embedded within the hump 323. A wire 318 is attached to the ball 314 and protrudes through the proximally-facing side of the hump 323 into the distal end 312 of the positioner 310. The other end of the wire 318 attaches to a second ball 317 embedded within the distal tip 312 of the positioner. Generally, the ball 317 is larger than the ball 315. To make the attachment, the ball 317 may be molded into a lumen 314 that passes through the positioner. The smaller ball 315, attached to the wire 318, may then be forced into a socket formed within the hump 323 of the electrode array. The distance $L_A$ from the distal tip 322 of the electrode array to the distal tip 312 of the positioner is about 3–5 mm. At least one pair of keeper tabs 313, or wings 313, are formed into the distal end of the positioner in order to form a channel into which the electrode array may pass, thereby keeping the positioner 310 in a desired alignment position alongside the electrode array 320. The electrode array 320 and positioner 310 may be made from any suitable materials as previously described, or as is known in the art. Typically, both the carrier of the electrode array 320 and the flexible positioner will be made from a suitable silicone polymer, such as LSR-70 and/or LSR-25. The balls 315 and 317, and the wire 318, may be made from platinum, or other suitable material.

Turning next to FIGS. 17 and 17A, another technique for attaching the distal end 312 of the positioner 310 to the electrode array 320 is illustrated. The positioner 310 shown in FIGS. 17 and 17A includes a first pair of wings 313 (or keeper tabs) located at its distal tip 312. These wings 313 are placed over the sides of the electrode array 320 at a position that is a distance $L_{A1}$ from the distal tip 322 of the electrode array. Typically, the distance $L_{A1}$ is about 3–5 mm. The inside of both wings 313 is glued, or otherwise attached, to the electrode array 320 at connection points 313' using a suitable bonding agent. The connection points 313' may be realized using just a drop or two of a suitable glue, or equivalent substance, e.g., LSR-25 (while in a liquid state) which thereafter is allowed to cure. It is desirable to form the connection points 313' so that they will break lose at a specified force, thereby allowing the positioner to be forcibly removed from the electrode array should the need arise to make such detachment, and with the break point always occurring at the attachment points 313'.

As seen in FIG. 17, the positioner 310 may also include a second pair of wings 315, or keeper taps, that are positioned 1–2 mm more proximally than the first pair of wings, or keeper tabs, 313. Such second pair of wings 311, when used, are not attached to the electrode array, but serve the keeping function described previously in connection with the positioners 150 and 160, i.e., they keep the positioner 310 in its desired position along the back side of the electrode array 320.

Advantageously, the positioner 310 and electrode array 320 used as components of the electrode system 300 depicted in FIGS. 15, 17 and 17A may be substantially the same as, and in most instances exactly the same as, the positioners 150 or 160, and the electrode array 10, described previously. This allows common manufacturing techniques and procedures to be used to make the electrode array and positioner regardless of the embodiment in which the electrode system components will eventually be used.

Figure 18A:
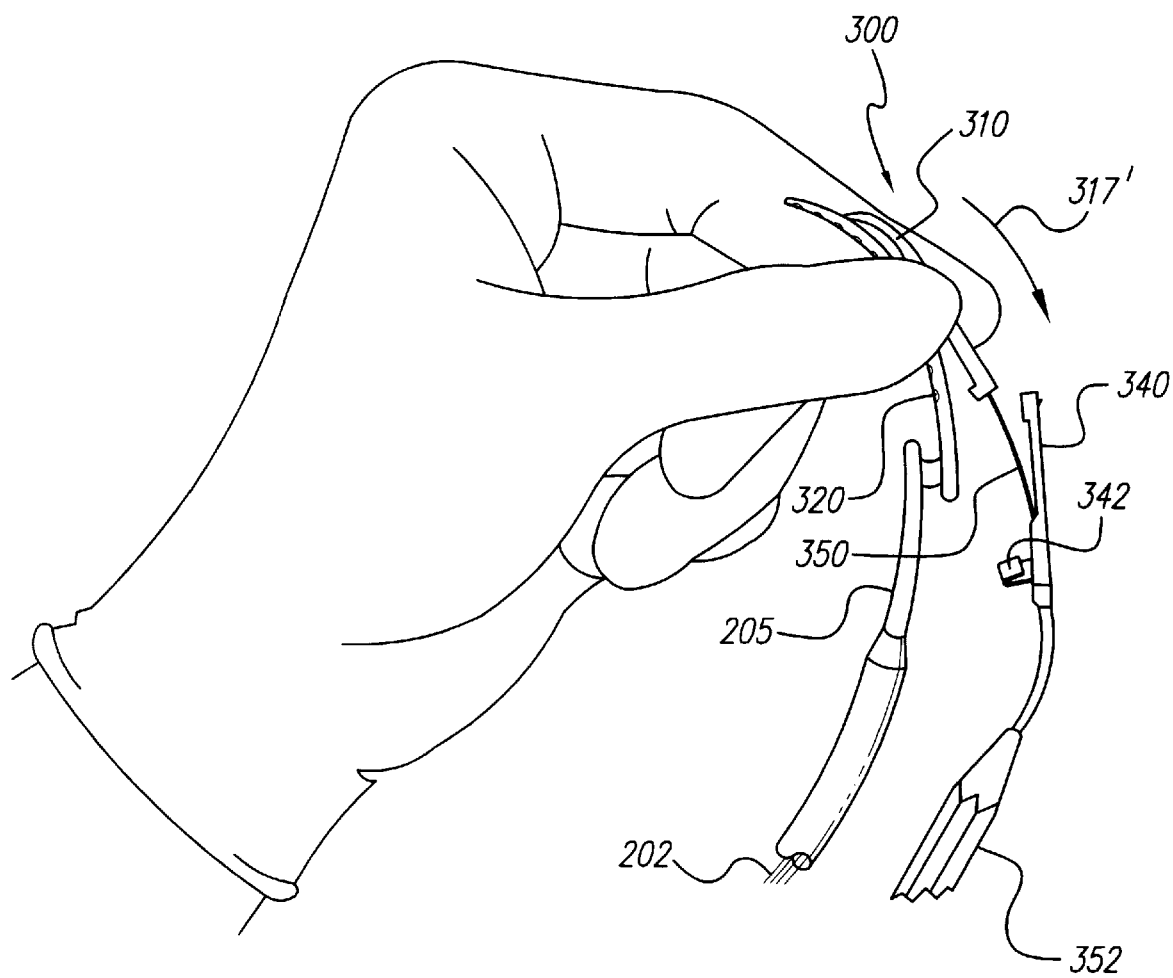
FIG. 18A illustrates loading the electrode system on a stylet wire used with an insertion tube prior to inserting the electrode system of FIG. 15 into the cochlea.

Another significant advantage associated with use of the electrode system 300 is that the electrode system may be inserted into the scala tympani of the cochlea in a one step operation. This is in contrast to the other electrode systems which usually require at least two steps (one step to insert the electrode, and another step to insert the positioner). The manner in which the one-step insertion is performed is illustrated in FIGS. 18A, 18B, 19, 20A, 20B and 20C. As seen in FIG. 18A, the electrode system 300 is loaded on a stylet wire 350 of a stylet insertion tool 352 by inserting the distal tip of the stylet wire 350 into the lumen 314 of the positioner 310. An insertion tube 340 is placed on a tip of the insertion tool 350, with the stylet wire 350 passing through a proximal tube portion 346 (FIG. 18B) of the insertion tube. The insertion tube 340 provides a U-channel into which the positioner 310 may reside, with the U-channel closing to a tube at the proximal tube portion 346. As the positioner 310 is threaded onto the stylet wire 350, a proximal end of the positioner 350 slides up against the tubular end portion of the insertion tube 340 while the body of the positioner is guided into the U-channel of the insertion tube. A hook 342 extends from the proximal end of the insertion tube 340. This hook 342 provides a location where the lead 205 from the electrode array 320 may be held during the insertion process. The positioner 310 (and hence the electrode system, because the positioner 310 is attached to the electrode array 320) is threaded onto the stylet wire 350 until the stylet wire 350 is fully inserted into the full length of the lumen 314 (essentially, the entire length of the positioner 310). This threading is done by pulling the positioner proximally (as depicted by arrow 317') over the stylet wire. When the stylet wire 350 is thus fully inserted into the lumen 314, the proximal end of the positioner is then resting against the tubular portion 346 of the insertion tube 340, as seen best in FIG. 18B. The lead 205 is then lifted onto the hook 342, completing the loading operation.

Figure 18B:
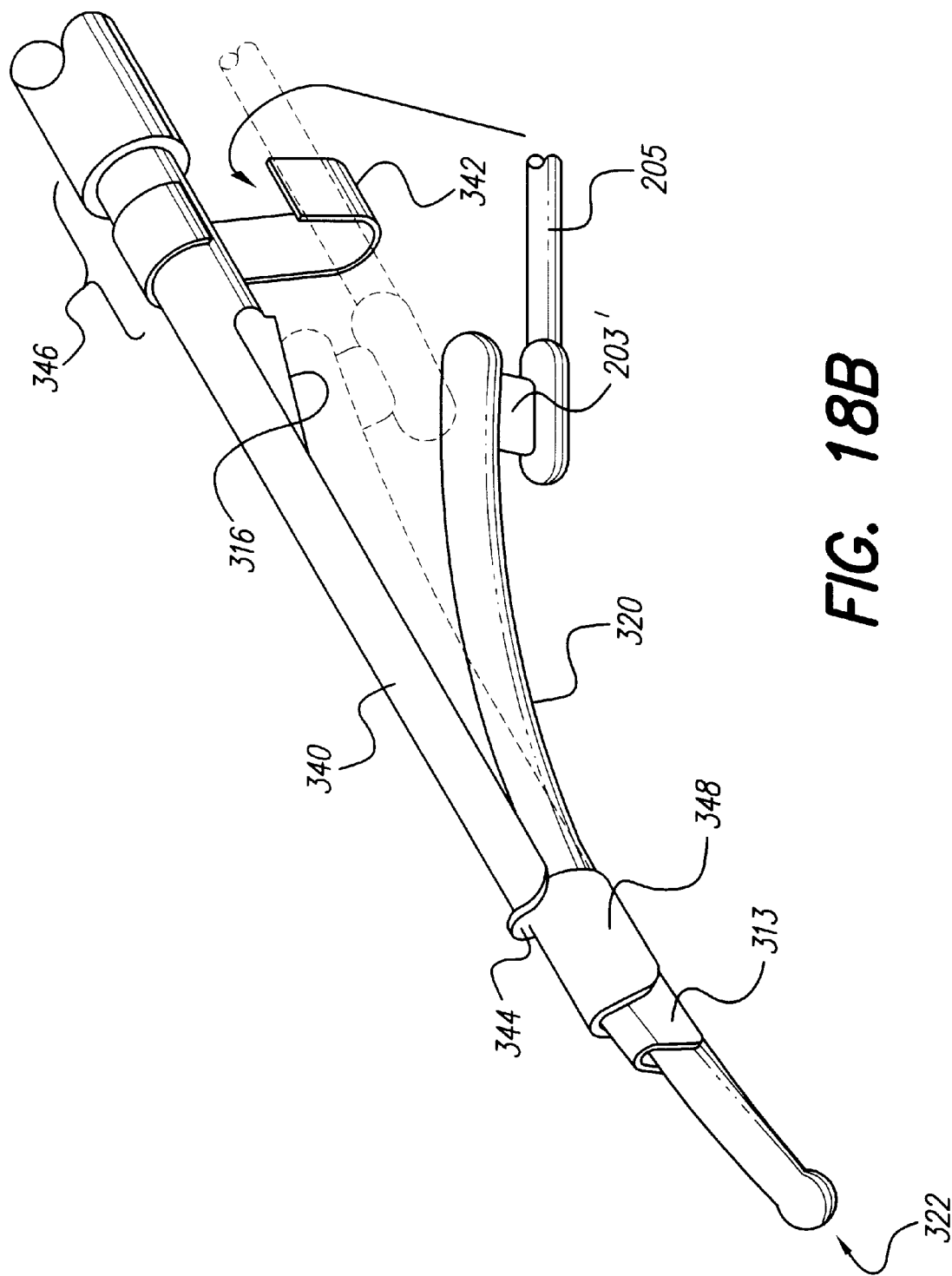
FIG. 18B shows an enlarged view of the electrode system of FIG. 15 as loaded into the insertion tube.
Figure 19:
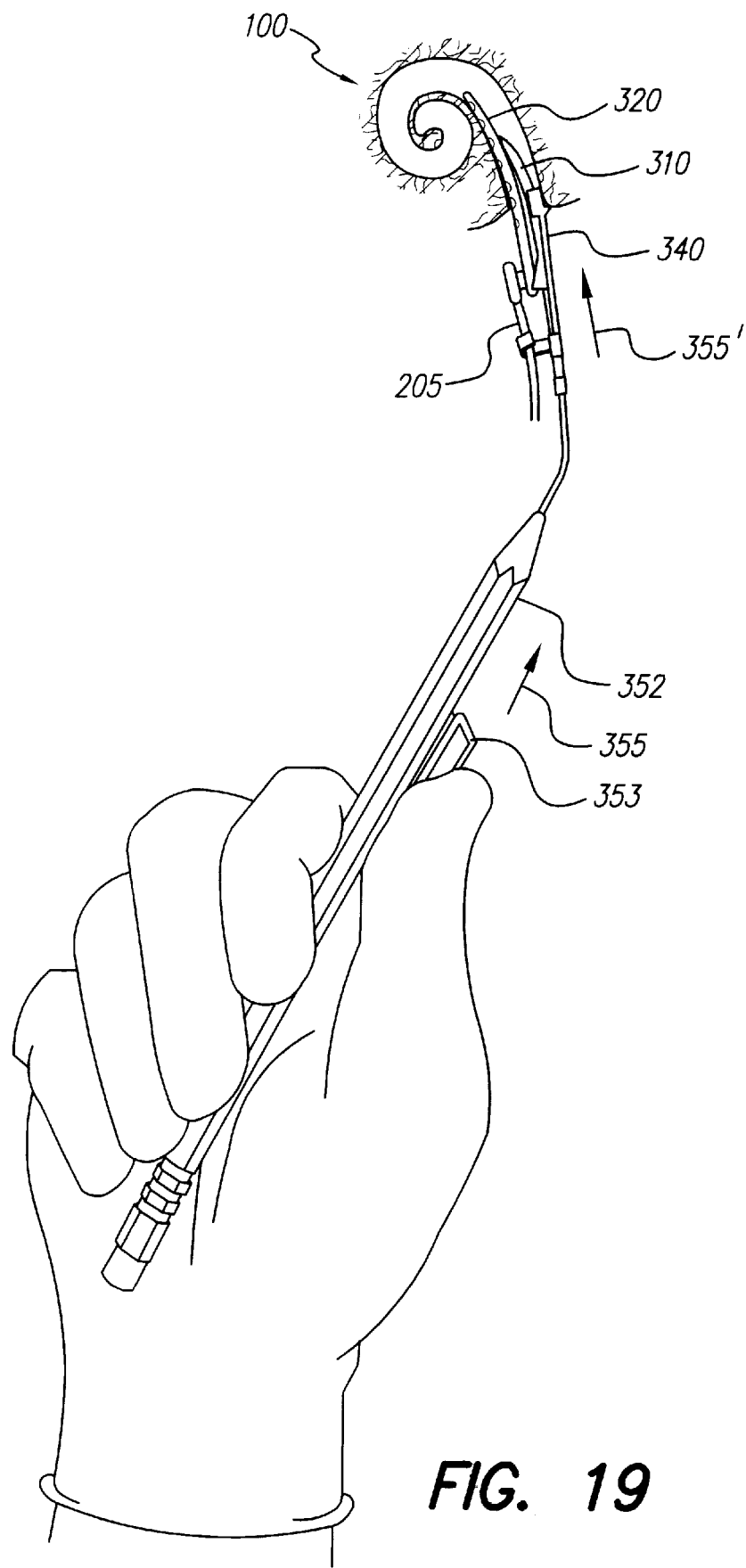
FIG. 19 illustrates use of the insertion tube to insert the electrode system of FIG. 15 into the cochlea through a cochleostomy made at the base of the cochlea in a one step operation.

With the electrode system 300 loaded into the insertion tube 340, and with the insertion tube placed onto the insertion tool 352, as shown in FIGS. 18A and 18B, the electrode system 300 is ready to be inserted into the cochlea 100 as seen in FIG. 19. Advantageously, such insertion may be carried out in one operation, i.e., both the electrode array 320 and the positioner 310 may be inserted into the cochlea at the same time with one simple motion of the insertion tool 352.

Figure 20A:
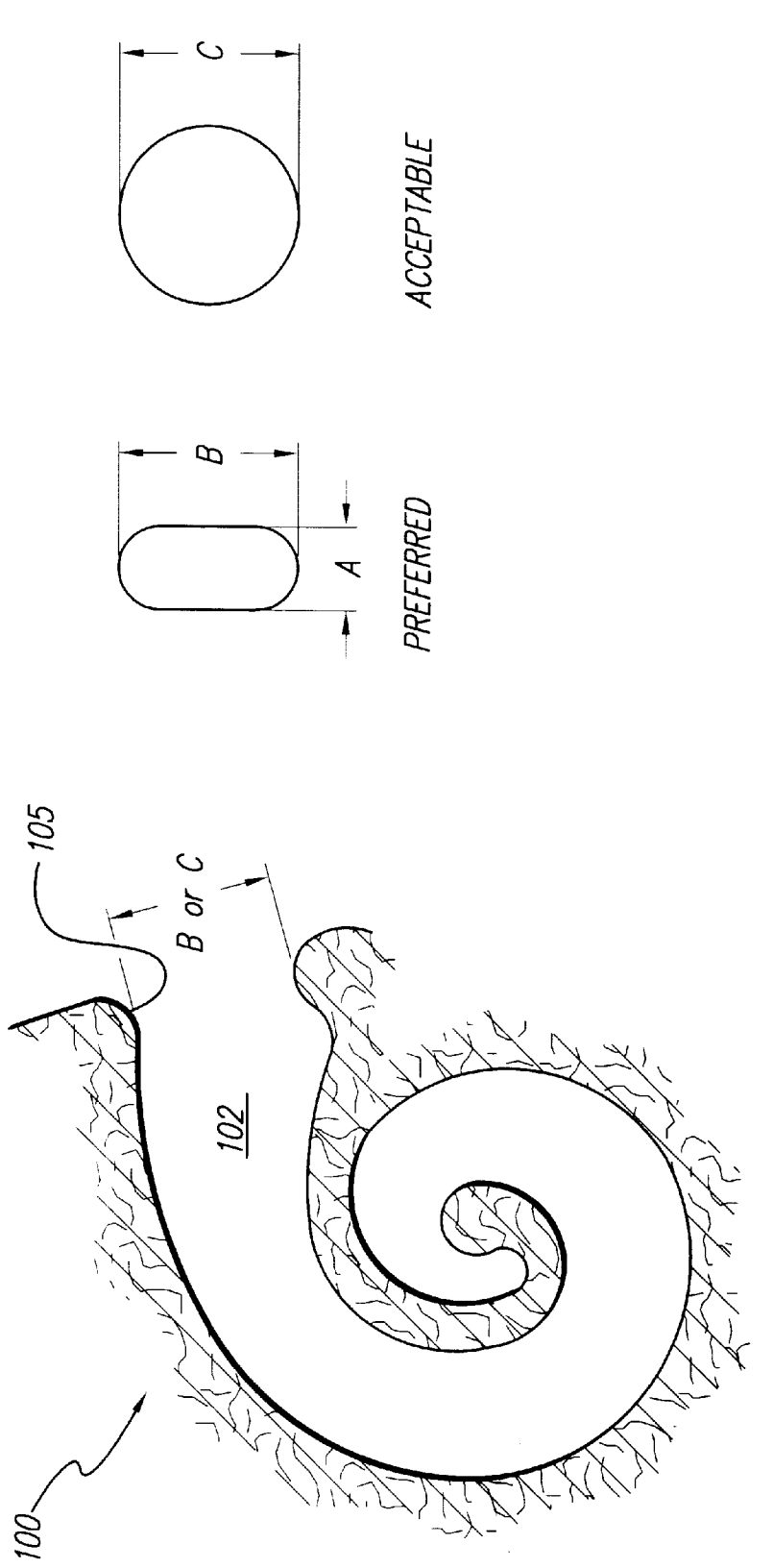
FIG. 20A illustrates the dimensions of the cochleostomy through which the electrode system is inserted as shown in FIG. 19.

The insertion of the electrode system 300 into the cochlea 100 is made through a cochleostomy 105 made at the basal end of the cochlea as shown in FIG. 20A. FIG. 20A further illustrates the approximate dimensions of the cochleostomy 105. As seen in FIG. 20A, an oval shaped opening, having a length, B, of about 2.0 mm and a width, A, of about 1.5 mm, is the preferred cochleostomy shape; but a round opening, having a diameter, C, of approximately 2.0 mm, is also suitable.

Figure 20B:
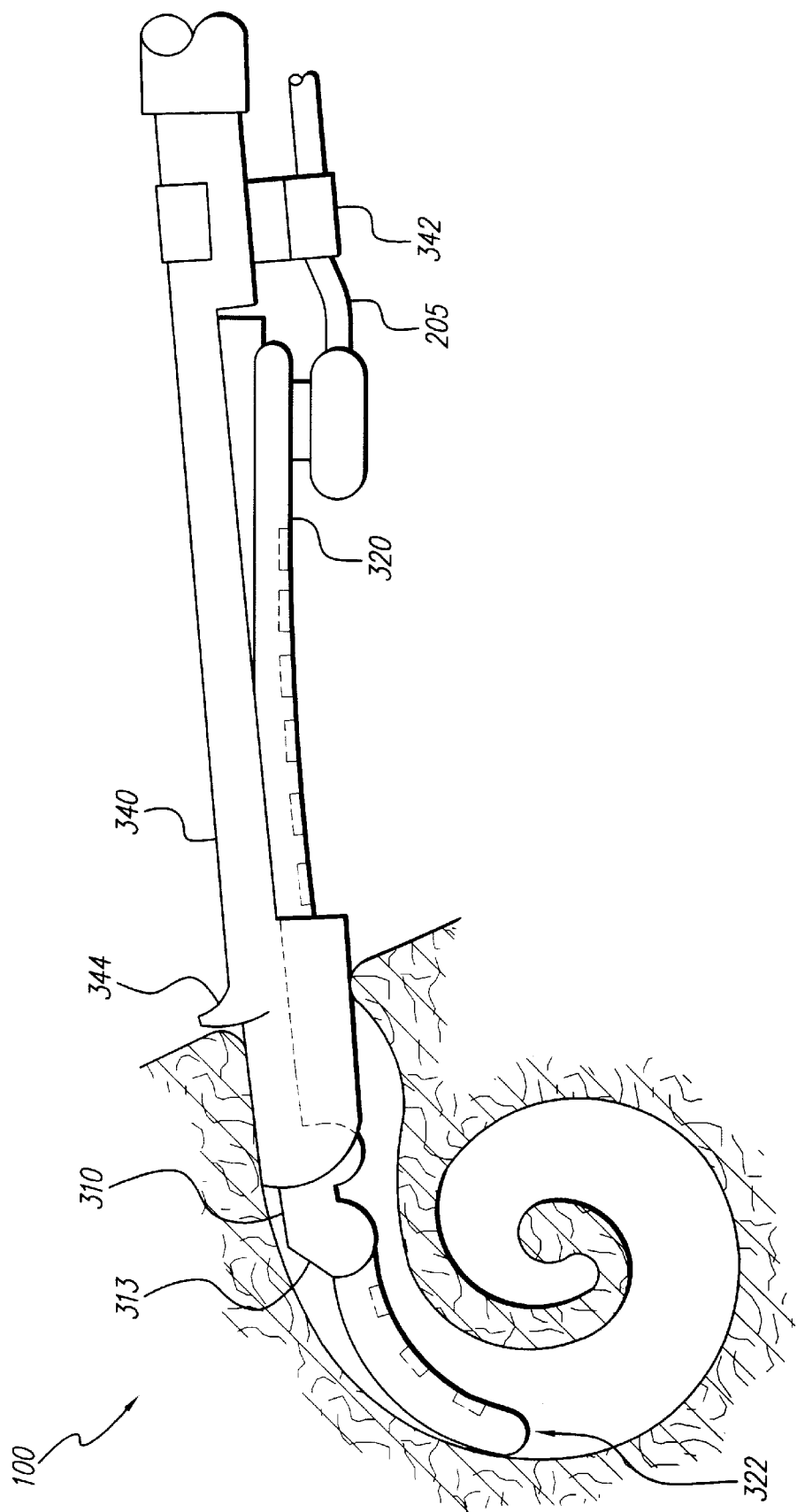
FIG. 20B is an enlarged view that details the placement of the insertion tube into the cochleostomy at the beginning of the insertion process.

As seen in FIGS. 19 and 20B, the insertion of the electrode system 300 into the cochlea begins by placing a tip of the insertion tube 340 into the opening made by the cochleostomy. A lip 344, near the distal end of the insertion tube 340, engages an edge of the opening created by the cochleostomy to hold the insertion tube at a proper depth within the cochlea. The physician moves a lever 353 on the insertion tool 352, which causes the stylet wire to move in a proximal direction, indicated by the arrow 355. Such movement of the stylet wire, in turn, causes the positioner 340, and hence the entire electrode system 300, to be carried distally into the cochlea, in the direction indicated by the arrow 355'. Advantageously, as the insertion force provided by motion of the stylet wire in the direction of the arrows 355 and 355' is transferred to the electrode system, it is applied to the electrode system at or near the distal tip 312 of the positioner, at the location where the positioner is attached to the electrode array 320. This means that the distal tip 322 of the electrode array may act as a flexible bumper, readily bending and maneuvering through the circuitous path of the scala tympani 102, without causing damage or trauma to the delicate cochlear structure.

Figure 20C:
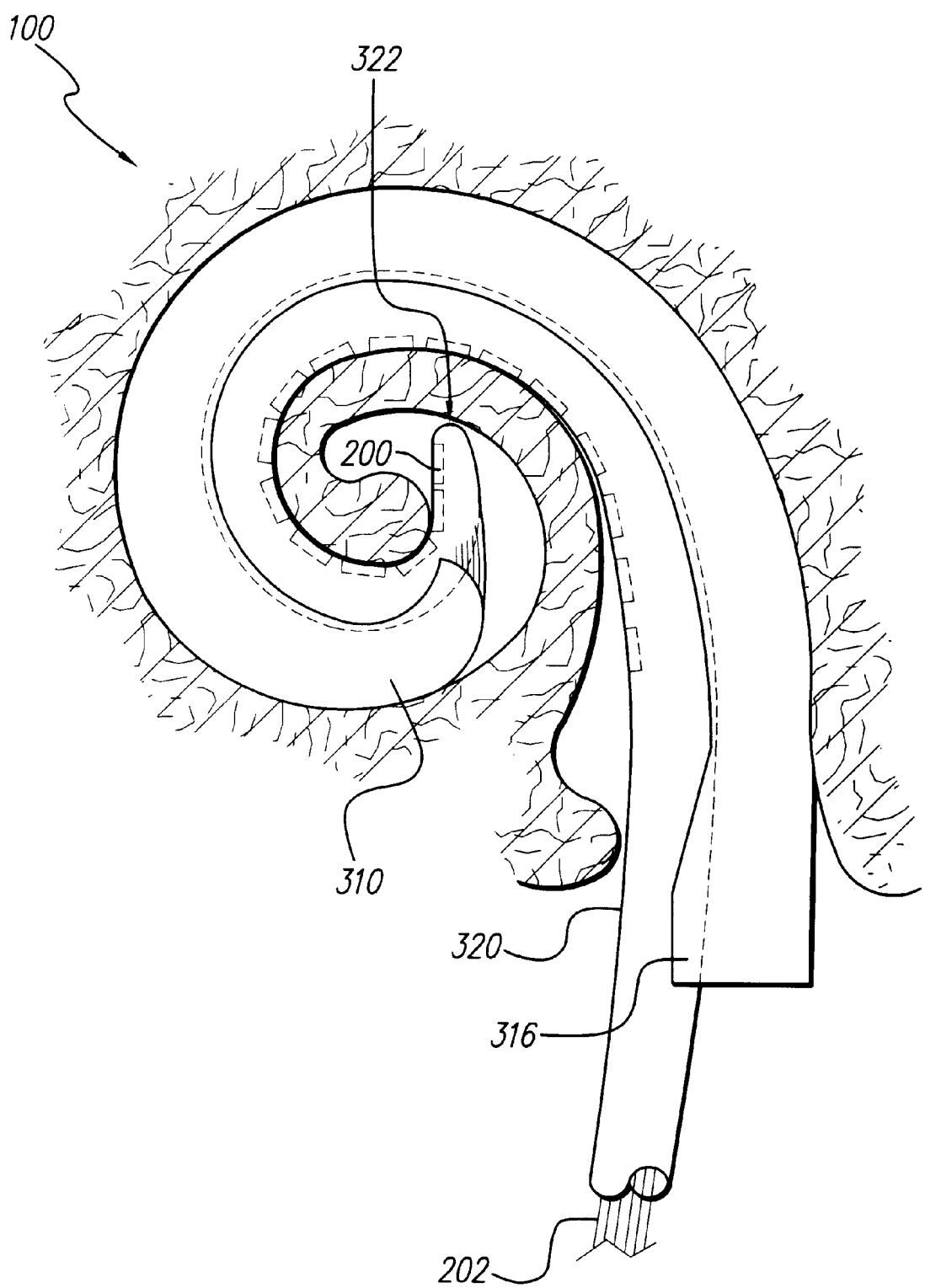
FIG. 20C shows a sectional view of the cochlea with the electrode system of FIG. 15 fully inserted therein, and further illustrates how the tapered wings at base of the positioner fix or lock the electrode array in the cochleostomy.

As the positioner is pushed deeper into the cochlea, as seen best in FIG. 20C, the positioner body fills the space behind the electrode array, causing the electrode array 320 to hug the modiolar wall 104. This hugging of the modiolar wall, with the front surface of the electrode array facing the modiolar wall, further places the electrode contacts 200 near, on in contact with, the modiolar wall, as desired. Upon full insertion of the electrode array and positioner into the cochlea, a sloping floor 152' between proximal side walls 316 (also known as "tapered wings") at the proximal end of the positioner, wedges the electrode array and positioner firmly into the cochleostomy, thereby holding the electrode system 300 in place within the cochlea.

FIGS. 21, 21A and 21B show various views of the insertion tube 340. The insertion tube 340 has a length L10, which is about 32 mm in length, has a proximal end portion 346, with a distance L11, which is about 9.4 mm in length, and a distal end portion 348, with a distance L12, which is about 4.0 mm in length. The insertion tube 340 may be made from stainless steel, or other suitable biocompatible metal or polymer. A preferred metal is the same metal used to make hypodermic needles. The proximal end portion 346 is a tube, having at least one transverse slit 347 formed therein. The rest of the insertion tube 340 is really not a tube, but a U-channel having a depth, L13, of 15 about 0.90 to 1.0 mm, except at a distal end portion 348, where the U-channel has a depth L14, of about 1.7 to 1.8 mm. The distal end 348 has long lobes 345 added to the U-channel to thereby create a deep U-channel. The deep U-channel is suitable for holding both the positioner and electrode array in a desired aligned position (with the positioner being held along the back side of the electrode array) as the two components are slidably inserted together into the cochlea near the base of the cochlea. The U-channel intermediate the deep U-channel distal end portion 348 and the proximal end tube portion 346 has a depth, L13, of about 0.9 to 1.0 mm, and may thus be considered as a shallow U-channel portion, and this shallow depth is suitable for holding the positioner as the insertion process pushes the electrode array deeper into the cochlea. As seen in FIG. 21A, the lip 344 wraps around the back of the U-channel an angle α2, where α2 is about 90°. The lip 344 may be made from a tube section that is laid over and spot welded to the U-channel. The lip 344 is preferably located a distance L15, where L15 is about 2.85 mm from the distal tip of the insertion tube. As seen in FIG. 21B, the positioner is preferably bent at a slight angle, e.g., about, L16, where L16 is about 1.5 mm or so off of a straight axis. That is, the insertion tube, when viewed from a side view with the open U-channel facing down, is bent to create a slight concave surface facing down.

The dimensions of the insertion tube 340 shown in FIGS. 21, 21A and 21B are not meant to be limiting, but are meant to be exemplary of suitable dimensions that may be used by those of skill in the art when making an insertion tube.

While the invention herein disclosed has been described by means of specific embodiments and applications thereof, numerous modifications and variations could be made thereto by those skilled in the art without departing from the scope of the invention set forth in the claims.

What is claimed is:

1. A cochlear electrode system comprising:
an electrode array comprising
a elongate flexible carrier having a distal end and a proximal end adapted to be inserted into a human cochlea,
a plurality of spaced-apart contacts carried by the flexible carrier,
a plurality of wires carried within the flexible carrier, at least one wire of the plurality of wires being electrically connected to one of the plurality of electrode contacts, each of the plurality of wires having a proximal end adapted to be coupled to electronic circuitry;
a positioner comprising an elongate flexible member having a distal tip and a proximal end adapted to be inserted into the human cochlea alongside the electrode array;
wherein the distal tip of the positioner is attached to the electrode array only near the distal end of the elongate flexible carrier and not at any other locations; and
wherein the positioner further has a first pair of keeper tabs protruding from the flexible member at a distal tip of the flexible member, and wherein one tab of the first pair of keeper tabs is attached to one side of the electrode array, and the other tab of the first pair of keeper tabs is attached to an opposite side of the electrode array, to thereby attach the distal tip of the positioner to the electrode array.

2. The cochlear electrode system of claim 2 wherein the positioner has a second pair of keeper tabs protruding from the flexible member near the first pair of tabs, wherein one tab of the second pair of keeper tabs is adapted to lie against one side of the electrode array, and the other tab of the second pair of keeper tabs is adapted to lie against an opposite side of the electrode array.

3. The cochlear electrode system of claim 2 wherein the tabs of the first and second pair of tabs are flexible, forming an integral part of the flexible member.

4. The cochlear electrode system of claim 1 wherein the distal tip of the positioner is attached to the electrode array at an attachment location that is 3–5 mm from the distal end of the elongate flexible carrier.

5. The cochlear electrode system of claim 4 further including an attachment wire connecting the distal tip of the positioner to the attachment location on the electrode array.

6. The cochlear electrode system of claim 5 wherein the attachment wire is attached at one end to a first ball embedded within the distal tip of the positioner and is attached at an opposite end to a second ball embedded within the elongate flexible carrier at the attachment location.

7. The cochlear electrode system of claim 4 wherein the distal tip of the positioner is attached to the attachment location on the electrode array by a bonding agent.

8. The cochlear electrode system of claim 1 wherein the positioner further includes a pair of side walls protruding from the flexible member near a proximal end of the positioner, and wherein one side wall of the pair of side walls is adapted to lie against one side of the proximal end of the electrode array, and the other side wall of the pair of side walls is adapted to lie against an opposite side of the proximal end of the electrode array, the space between the side walls defining a proximal channel adapted to receive the proximal end of the electrode array, the proximal channel being adapted to keep the proximal end of the positioner alongside the proximal end of the electrode array when the positioner is inserted into the cochlea.

9. The cochlear electrode system of claim 8 wherein the proximal channel has a depth that varies from a first depth at the proximal end of the proximal channel to a second depth at a distal end of the proximal channel, the depth being measured as the distance from a floor of the proximal channel to a top edge of the side wall.

10. The cochlear electrode system of claim 1 wherein the positioner has an opening passing longitudinally therethrough, the opening being adapted to receive a stylet wire when the positioner is being inserted into the cochlea.

11. The cochlear electrode system of claim 10 wherein the opening passing longitudinally through the positioner is closed at the distal tip of the positioner.

12. The cochlear electrode system of claim 11 further including a metal marker sealed in the closed end of the opening that passes longitudinally through the positioner, wherein the metal marker provides an identifiable reference location detectable through an imaging system.

13. A cochlear electrode system adapted for insertion into a cochlea comprising:
an electrode array having a distal tip,
a positioner attached to the electrode array at an attachment location that is 3–5 mm from the distal tip of the electrode array.

14. The cochlear electrode system of claim 13 further comprising
a removable insertion tube; and
a stylet insertion tool having a movable stylet wire therein;
wherein the movable stylet wire is adapted to pass through the removable insertion tube and engage with the positioner when the electrode system is inserted into the cochlea.

15. The cochlear electrode system of claim 14 wherein the positioner has a lumen passing longitudinally through the positioner, wherein the lumen is closed at a distal end of the lumen, and wherein the lumen is adapted to receive the stylet wire when the electrode system is inserted into the cochlea.

16. The cochlear electrode system of claim 15 wherein the insertion tube comprises a proximal tube portion, a distal deep U-channel portion, a shallow U-channel portion intermediate the proximal tube portion and the distal deep U-channel portion, and a lip formed on a back side of the deep U-channel portion about 2–3 mm from the distal end of the insertion tube.

17. The cochlear electrode system of claim 16 wherein the insertion tube, when viewed from a side view with the open U-channel facing down, is bent to create a concave surface facing down.

18. The cochlear electrode system of claim 16 wherein the insertion tube has a hook attached to the proximal tube portion thereof, the hook providing a means for temporarily holding a lead adapted to be attached to the electrode array during an insertion process.

19. A cochlear electrode system comprising:
an electrode array comprising an elongate flexible carrier body having a distal end, a proximal end, and a plurality of spaced-apart electrode contacts along one surface of the carrier body;
a positioner, the positioner having a distal end that is attached to the elongate flexible carrier body of the electrode array at an attachment location that is 3–5 mm from the distal end of the flexible carrier body, wherein the positioner has a lumen passing longitudinally therethrough, the lumen being closed at its distal end.

* * * * *